US007627938B2

(12) United States Patent
Kim et al.

(10) Patent No.: US 7,627,938 B2
(45) Date of Patent: Dec. 8, 2009

(54) TAPERED HOLLOW METALLIC MICRONEEDLE ARRAY ASSEMBLY AND METHOD OF MAKING AND USING THE SAME

(75) Inventors: Kabseog Kim, Urbana, IL (US); Jeong-Bong Lee, Plano, TX (US)

(73) Assignee: Board of Regents, The Univeristy of Texas System, Austin, TX (US)

( * ) Notice: Subject to any disclaimer, the term of this patent is extended or adjusted under 35 U.S.C. 154(b) by 274 days.

(21) Appl. No.: 10/966,987

(22) Filed: Oct. 15, 2004

(65) Prior Publication Data

US 2006/0084942 A1 Apr. 20, 2006

(51) Int. Cl.
*B23P 25/00* (2006.01)

(52) U.S. Cl. .......................... 29/458; 29/17.3; 604/272; 604/290

(58) Field of Classification Search .................... 29/458, 29/17.3; 604/27, 272, 290, 890.1
See application file for complete search history.

(56) References Cited

U.S. PATENT DOCUMENTS

| | | | |
|---|---|---|---|
| 4,578,770 A | 3/1986 | Mitani | |
| 4,596,792 A | 6/1986 | Vyas | |
| 4,599,230 A | 7/1986 | Milich et al. | |
| 4,599,231 A | 7/1986 | Milich et al. | |
| 4,601,903 A | 7/1986 | Frasch | |
| 4,608,251 A | 8/1986 | Mia | |
| 5,591,139 A | 1/1997 | Lin et al. | |
| 6,334,856 B1* | 1/2002 | Allen et al. | .................. 604/191 |
| 6,406,638 B1 | 6/2002 | Stoeber et al. | |
| 6,503,231 B1* | 1/2003 | Prausnitz et al. | ............ 604/272 |
| 6,511,463 B1* | 1/2003 | Wood et al. | .................. 604/272 |
| 6,551,849 B1* | 4/2003 | Kenney | ....................... 438/34 |
| 6,565,532 B1* | 5/2003 | Yuzhakov et al. | ........... 604/142 |
| 6,692,680 B2 | 2/2004 | Lee et al. | |
| 6,748,954 B2 | 6/2004 | Lee et al. | |
| 2002/0133129 A1* | 9/2002 | Arias et al. | .................. 604/272 |
| 2002/0155737 A1* | 10/2002 | Roy et al. | ...................... 439/66 |
| 2005/0011858 A1* | 1/2005 | Kuo et al. | ...................... 216/17 |
| 2005/0137531 A1* | 6/2005 | Prausnitz et al. | ............ 604/173 |
| 2006/0015061 A1* | 1/2006 | Kuo et al. | ...................... 604/47 |

OTHER PUBLICATIONS

Kim et al, "A Tapered Hollow Metallic Microneedle Array using Backside Exposure of SU-8", Journal of Micromechanics and Microengineering, Published Feb. 6, 2004 [all].*

Kuo et al., "A Novel Polymer Microneedle Arrays and PDMS Micromolding Technique", Tamkang Journal of Science and Engineering, vol. 7, No. 2, pp. 95-98 (2004), Published Feb. 2004.*

(Continued)

*Primary Examiner*—Jermie E Cozart
*Assistant Examiner*—Christopher M Koehler
(74) *Attorney, Agent, or Firm*—Chainey P. Singleton; Edwin S. Flores; Chalker Flores, LLP

(57) ABSTRACT

The present invention includes device, system, method of using and making a microneedle array including the steps of forming one or more pins on a substrate, depositing one or more layers on the one or more pins and the substrate, exposing a portion of the one or more pins, and separating the one or more pins from the one or more layers to form the hollow microneedle array.

28 Claims, 11 Drawing Sheets

OTHER PUBLICATIONS

Ahn, C., et al., "Disposable smart lab-on-a-chip for point-of-c may be clinical diagnostics," Proc. 2004, IEEE, pp. 92154-92173.

Chandrasekaran, S., et al., "Characterization of surface micromachined metallic microneedles," J.MEMS, 2003, pp. 12288-12295.

Kabseog Kim, et al., "A tapered hollow metallic microneedle array using backside exposure of SU-8," 2004, Journal of Micromechanics and Microengineering, vol. 14, No. 4, pp. 597-603.

Kabseog Kim, et al., "Rapid replication of polymeric and metallic high aspect ratio microstructures using PDMS and LIGA technology," 2001, Microsystem Technologies, vol. 9, No. 1-2, pp. 5-10.

Lin, L., et al., "Silicon-processed microneedles," J.MEMS 1999, pp. 878-884.

McAllister, D. V., et al., "Three-dimensional hollow microneedle and microtube arrays" 10th Int. Conf. Solid-State Sensors and Actuators 1999, pp. 1098-1101.

S. W. Park, et al., "Massive replication of polymeric high aspect ratio microstructures using PDMS casting," in Proceedings of the SPIE 2001 Smart Electronics and MEMS, Mar. 2001, SPIE vol. 4334, pp. 271-279 Newport Beach, CA.

Zimmermann, S., et al., "A microneedle-based glucose monitor: fabricated on a wafer-level using in-device enzyme immobilization," 12th Int. Conf. Solid-State Sensors and Actuators, 2003, pp. 99-102.

* cited by examiner

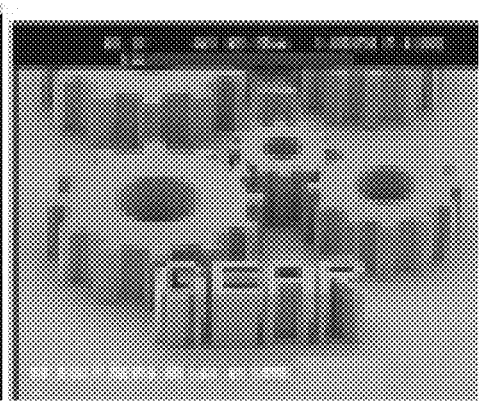
FIG. 8A  FIG. 8B
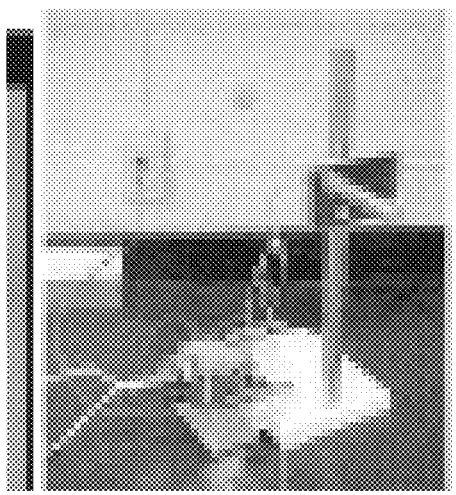
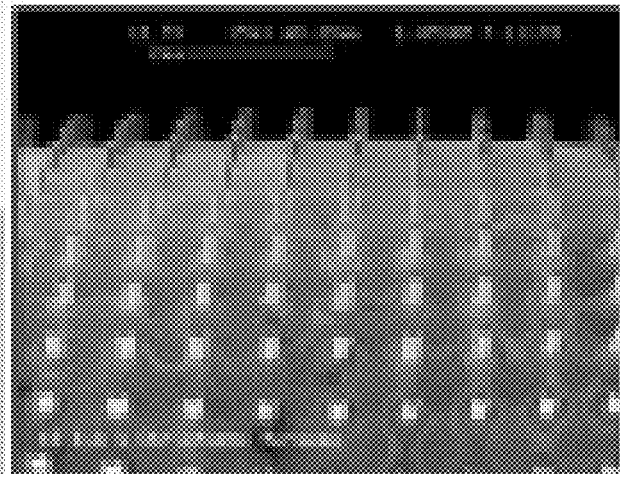
FIG. 8C  FIG. 8D

TAPERED HOLLOW METALLIC MICRONEEDLE ARRAY ASSEMBLY AND METHOD OF MAKING AND USING THE SAME

The U.S. Government may own certain rights in this invention pursuant to the terms of the DARPA Grant No. F30602-00-1-0569. Without limiting the scope of the invention, its background is described in connection with devices and methods for transporting therapeutic or biological molecules across barriers.

TECHNICAL FIELD OF THE INVENTION

The present invention relates in general to the field of transporting compounds across a barrier and, more particularly, to devices and methods for transporting therapeutic or biological molecules across or through a tissue barrier, such as for drug delivery or sampling of biological fluids.

BACKGROUND OF THE INVENTION

Currently, research and development has been directed to the development of new drugs and therapeutic agents to battle a variety of illness and diseases. Frequently, the nature of these new drugs and therapeutic agents limit the method of delivery that may be used to deliver the agent (e.g., the skin, the oral mucosa, the gastrointestinal tract, the blood-brain barrier). Additionally, the rate of transport of the new drugs and therapeutic agents may be less than optimal or effective and are therapeutically ineffective. Therefore, it is necessary to develop alternative delivery techniques.

Drugs may be commonly administered in a variety of ways e.g., orally as liquids, pills or capsules, across a biological barrier as syringes, transdermal patch or catheters, however these methods of delivery each have limitations and disadvantages. Orally administered drugs or therapeutic agents may face degradation in the gastrointestinal tract and/or elimination by the liver and thus, limit the efficiency of the treatment. Additionally, some drugs or therapeutic agents cannot effectively diffuse across the intestinal mucosa rendering them ineffective. Often oral treatments require administering treatment at particular intervals over a prolonged time, which raise the issue of patient compliance.

Another common method of delivering drugs or therapeutic agents across a biological barrier is by using a needle (e.g., standard syringes or catheters) to transport drugs through the skin. The use of needles is inconvenient for the patient, and often painful, particularly when frequent samples are required, e.g., diabetic patients. The invasiveness of methods involving conventional needles results in pain; local damage to the skin at the site of insertion; bleeding that increases the risk of disease transmission; and a wound sufficiently large enough to be a site of infection. In some cases, needle treatments are too painful and inconvenient or impractical for continuous controlled drug delivery over a period of hours or days. Additionally, needle phobias may result that lead to a significant risk to the life and health from the avoidance of medical or dental care. Therefore, methods using conventional needles for drug delivery is undesirable for prolonged treatments due to vascular damage caused by repeated punctures (e.g., as a result of a diabetic's delivery of insulin). Furthermore, needle techniques often require administration by a person trained in its use.

In addition to administering agents across a biological barrier, needles may be often used to withdraw biological substances from one side of a biological barrier, e.g., bodily fluids, such as for diagnostic purposes or sampling of biological fluids (e.g., diabetic's blood glucose sampling). The invasiveness of withdrawing samples using conventional needles results in pain; local damage to the skin at the site of insertion; bleeding that increases the risk of disease transmission; and a wound sufficiently large enough to be a site of infection. Less painful methods for obtaining a sample are known, such as lancing the arm or thigh, which have a lower nerve ending density, however sampling of such areas often result in inadequate results as those locations are not heavily supplied with near-surface capillary vessels. Currently, no alternative methodologies are available to address these problems. Proposed alternatives to the conventional needle, require the use of lasers or heat to create a hole in the skin, which is inconvenient, expensive, and/or undesirable for repeated use.

Another delivery technique includes the use of a transdermal patch, which usually relies on diffusion of the drug across the skin. However, the reliance on diffusion and skin barrier permeability (i.e., effective barrier properties) limits the substances, which may be administered by transdermal diffusion as a function of substance size, hydrophilicity and the concentration gradient across the barrier. Few compounds possess the necessary physiochemical properties to be effectively delivered through the skin by the passive diffusion of a transdermal patch.

Active diffusion techniques (e.g., iontophoresis, electroporation, ultrasound, and heat) have been used in an attempt to improve the rate of delivery. However, these techniques may be not suitable for all types of drugs, failing to provide the desired level of delivery efficiency. Additionally, these techniques may also be impractical, inconvenient and/or painful.

For example, U.S. Pat. No. 6,565,532 to Yuzhakov, et al., discloses a "Microneedle apparatus for marking skin and for dispensing semi-permanent subcutaneous makeup." The microneedles disclosed can apply identifications or other tattoo-like graphics, and will not enter into the dermal layer of the skin so that the application procedure is painless. The microneedle array is also useful for delivering specific compounds or actives into the skin, such as cosmetic compounds or nutrients, or various skin structure modifiers that can be delivered subcutaneously without having to visit a cosmetic surgery clinic. The invention disclosed in the patent provides a method for manufacturing an array of microneedles using standard semiconductor fabrication techniques like silicon etching by which a silicon substrate was etched to create hollow or solid individual microneedles. Other micromolding methods including LIGA and deep LIGA processes and hot embossing and microinjection methods were used to fabricate polymeric microneedle arrays.

In another example, U.S. Pat. No. 6,503,231 to Prausnitz, et al., discloses a "Microneedle device for transport of molecules across tissue" and U.S. Pat. No. 6,334,856 to Allen, et al., discloses a "Microneedle device and methods of manufacture and use thereof." The patents relate to methods for manufacturing an array of microneedles, which may be hollow and/or porous and have diameters between about 10 nm and 1 mm, fabricated by microfabrication techniques from metals, silicon, silicon oxide, ceramic, and polymeric materials. A reactive ion etch process is used to etch silicon with gas mixtures of $SF_6$ and $O_2$ to make tapered and sharp Si master mold, and then $SiO_2$ or metal was deposited to form hollow microneedles. Finally, the hollow microneedle arrays were released from the silicon substrate by wet etching or dry etching. Further similar vertical hollow microneedles were created by resist patterning combined with underetching. With Si spikes, SU-8 resist casting method was used to make SU-8 mold and electroplating metals onto the SU-8 mold and removal of the SU-8 mold generated the tapered hollow metallic microneedles.

U.S. Pat. No. 6,511,463 Wood, et al., discloses methods of fabricating microneedle arrays using sacrificial molds and relates to methods of fabricating hollow vertical microneedle or tube arrays by use of multiple steps of molding with a master mold and a sacrificial mold. The patent discloses a microneedle array fabricated by providing a sacrificial mold including a substrate and an array of posts, preferably solid posts, projecting therefrom. A first material is coated on the sacrificial mold including on the substrate and on the array of posts. The sacrificial mold is removed to provide an array of hollow tubes projecting from a base.

What is need is a cost effective method of fabricating a delivery mechanisms that is relatively painless and facilitates transport of a variety of therapeutic or biologically active molecules across tissue barriers, such as for drug delivery or sampling of biological fluids.

SUMMARY OF THE INVENTION

It would therefore be desirable and very useful to develop a relatively painless needle device for delivery of drugs across or into biological tissue, which permits drug delivery at clinically relevant rates across or into skin or other tissue barriers, with minimal or no damage, pain or irritation to the tissue. The present invention provides a therapeutic agent delivery device and sampling apparatus that is convenient and relative painless, particularly when frequent samples are required, e.g., diabetic patients. The present invention provides a less invasive method of delivery or sampling resulting in less pain; less local damage to the skin at the site of insertion; less bleeding which in turn decreases the risk of disease transmission; and a relative small wound reducing the possibilities of infection.

The hollow microneedle array device of the present invention is a convenient and effective alternative for the administration of many types of medications, including anti-anginals (e.g., nitroglycerin), hormones (e.g., estrogens) and antihypertensives (e.g., cloncidine). A hollow microneedle array device is beneficial because the agents are delivered directly into the blood stream, avoiding first-pass metabolism in the liver, so that drug delivery is continuous and sustained. Additionally, the present invention may be used in the administering of vaccines for use in both active and passive immunization. The hollow microneedle array may also be used to provide a sustained and consistent delivery of medication, avoiding peaks and valleys in blood levels which are often associated with oral dosage forms and which are usually undesirable. Thus, using a hollow microneedle array, one can administer lower doses of drug to achieve the same therapeutic effect compared to oral administration, reducing or eliminating dose-dependent side effects.

The present invention uses backside exposure to form a tapered hollow microneedle array to provide a high quality transdermal drug delivery and sampling device. The present invention has a great potential to be used as a critical component of a fully integrated miniaturized disposable clinical diagnostics system. The tapered hollow microneedle array of the present invention may be used in administering, treating, sampling, evaluate or even diagnosing conditions. The present invention provides a method to make a hollow microneedle array that includes the steps of forming one or more pins on a substrate, depositing one or more layers on the one or more pins and the substrate, exposing a portion of the one or more pins and separating the one or more pins from the one or more layers to form the hollow microneedle array.

The substrate used in the present invention may be a generally transparent substance including glass, plastic, polymer, or combinations thereof. The substrate may include one or more agents that are bioactive, biodegradable, electrically conductive, thermally conductive, porous, stimulatable, or combinations thereof. A release layer may be applied between the one or more pins and the substrate. Addition release layers may be applied between the one or more pins and the one or more layers either separately or in conjunction with the release layer applied between the one or more pins and the substrate. In one embodiment, the release layer may be a SU-8 release layer. In other embodiments, the release layer includes one or more of Si, a silicon nitride composition (SiNx), a silicon oxide composition (SiOx), or titanium (Ti) deposited between the substrate and the first layer, between layers or combinations thereof.

The one or more layers may be deposited through a variety of methods including, e.g., electroplating, vapor deposition, spin coating, coating, sputtering, in-situ polymerization or combinations thereof The one or more layers may be a metal, a nonmetal, a polymer, a composite, a resist, a resin, a carbon nano-tube, a plastic or combinations thereof. Additionally, the one or more layers may be bioactive, biodegradable, electrically conductive, thermally conductive, porous, stimulatable, or combinations thereof.

In one embodiment of the present invention nickel may be used as a material for layer of the microneedle arrays; however, other metals or metal containing compounds may be used, e.g., gold, silver, platinum, copper, aluminum, tungsten, titanium, tantalum, molybdenum, chromium, nickel or the like, alloy thereof or combinations thereof. The metal compound may be titanium nitride, titanium tungsten, tantalum nitride, tungsten nitride, molybdenum nitride or the like.

In accordance with the present invention, a wide variety of photoimagable polymers may be used such as photoimagable polyimides, photoimagable benzocyclobutenes, photoimagable epoxies, novolac based positive photoresists, cardo type photopolymers, and the like. Difunctional epoxy compounds may also be used including diglycidyl ethers of Bisphenol A (e.g., those available under the trade designations "Epon 828", "Epon 1004", "Epon 1001F", "Epon SU-8" and "Epon 1010" from Shell Chemical Co., "DER-331", "DER-332", and "DER-334" from Dow Chemical Co.), 3,4-epoxycyclohexylmethyl-3,4-epoxycyclohexene carboxylate (e.g., "ERL-4221" from Union Carbide Corp.), 3,4-epoxy-6-methylcyclohexylmethyl-3,4-epoxy-6-methyl-cyclohexene carboxylate (e.g., "ERL-4201" from Union Carbide Corp.), bis(3,4-epoxy-6-methylcyclohexylmethyl) adipate (e.g., "ERL-4289" from Union Carbide Corp.), bis(2,3-epoxycyclopentyl) ether (e.g., "ERL-0400" from Union Carbide Corp).

Additionally, some embodiments may use polymers that may be biodegradable. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone).

Another method of the present invention may include the step of introducing one or more agents into a portion of the microneedle array. A variety of agents may be used including but not limited to steroids, respiratory agents, sympathomimetics, local anesthetics, antimicrobial agents, antihypertensive agents, antihypertensive diuretics, cardiotonics, coronary vasodilators, vasoconstrictors, beta-blockers, antiarrhythmic agents, calcium antagonists, anti-convulsants, agents for dizziness, tranquilizers, antipsychotics, muscle relaxants, drugs for Parkinson's disease, non-steroidal hormones, antihormones, vitamins, antitumor agents, miotics, herb medicines, antimuscarinic, muscarinic cholinergic blocking agents, mydriatics, psychic energizers, humoral agents, antispasmodics, antidepressant drugs, anti-diabetics, anorectic drugs, anti-allergenics, decongestants, antipyretics, antimigrane, anti-malarials, anti-ulcerative, peptides, anti-estrogen, anti-hormone agents, antiulcer agents, anesthetic agent, drugs having an action on the central nervous system or combinations thereof. Furthermore, the one or more agents may be in the form of a solid, a liquid or a gas and may occupy an individual volume or combined volume of between 0.01 µl and 1.0 ml.

The present invention provides a method of making a microneedle array, wherein the steps of forming one or more pins further include the steps of applying one or more resist layers to the substrate, masking a portion of a resist layer and irradiating the resist layer, whereby the unmasked portion of the resist layer is irradiated and thus forms an optically cured resist layer. The method further includes the steps of applying a second resist layer to the cured resist layer, whereby the second resist layer provides an area to form the one or more pins, masking a portion of the second resist layer and irradiating through the unmasked portion of the second resist layer and the backside of the cured resist layer, whereby the second resist layer is optically cure forming one or more pins in the second resist layer. The unmasked portion of the resist layer may be generally circular in geometry and between about 20 and 120 µm diameter. However, persons of ordinary skill in the art will recognize that other shapes (e.g., oval, square, rectangular, polygonal and the like) and sizes (e.g., 1-10, 10-20, 120-200, 200-300, 300-400, 400-500, 500-1000 µm) may also be used.

The one or more optically cured pins may be coated by the deposition of one or more layers through a variety of methods including e.g., electroplating, vapor deposition, spin coating, coating, sputtering, in-situ polymerization or combinations thereof. The one or more layers may be a metal, a nonmetal, a polymer, a composite, a resist, a resin, a carbon nano-tube, a plastic or combinations thereof. Additionally, the one or more layers may be bioactive, biodegradable, electrically conductive, thermally conductive, porous, stimulatable, or combinations thereof.

The present invention provides the additional step of applying a resist layer to the one or more deposited layers, whereby the resist layer covers the one or more deposited layers and the substrate. In some embodiments, the one or more deposited layers may be a resist, whereby the resist layer covers the one or more deposited layers and the substrate. The one or more pins produced by the method of the present invention may have a tip that is pointed, rounded, slanted, flared, tapered or blunt. The pins of the microarray may have tips, which may be similar to each other or different. A portion of the pin may be exposed, the exposed portion may be on one side of the one or more pins, on the tip of the one or more pins or combinations thereof. The exposed portion may be exposed through a variety of techniques including mechanical mechanisms (e.g., grinding/etching, laser ablation or chemical-mechanical polishing (CMP)) and chemical removal to planarize the surface.

One method of the present invention provides the additional step of etching the microneedle array, whereby a hollow structure remains. The product made by this process includes an array of hollow pins that are between about 200 and 400 µm in height. However, other heights may be produced as well (e.g., between 10 and 200, 400 and 600, 600 and 800, 800 and 1000 µm). The thickness of a wall of the hollow pins of the microneedle array may be between about 1 and 10 µm, 10 and 20 µm, 20 and 30 µm, 30 and 40 µm, 40 and 50 µm, 50 and 60 µm, 60 and 70 µm, 70 and 80 µm, 80 and 90 µm, and 90 and 100 µm.

Another embodiment of the present invention includes a method of making a microneedle array including the steps of forming one or more pins on a substrate, depositing one or more layers including a conducting portion on the one or more pins and the substrate, exposing a portion of the one or more pins and separating the one or more pins from the one or more layers to form the hollow microneedle array. The conducting portion may be a wire, molecular wire, polymer, nano-tube, inorganic compound, semiconductor particle, fiber optics or combinations thereof. The method may include the additional step of disposing one or more agents in or about the microneedle array.

The present invention provides a device for transmitting one or more agents to a patient including a microneedle array and one or more agents located in or about the microneedle array. The device may further include a delivery mechanism, wherein the one or more agents are delivered to the patient. The delivery mechanism may be activated by tension, manually, shear force, diffusion, injection, pressure, electrostatic, osmosis, concentration gradients, electrical magnetic field, low frequency ultrasound or combinations thereof. The delivery mechanism may be controlled by a feedback system or other control mechanism known to persons of ordinary skill in the art. The one or more agents may be delivered to the patient thought the one or more needles, whereby the one or more agents pass through the one or more needles.

The microneedle array may also include one or more exposed portions wherein one or more agents may be delivered through the one or more exposed portions, to the patient. However, the one or more agents may be deposited externally on or about the microneedle array, allowing the agent to be delivered through diffusion. Additionally, the one or more agents may be deposited within one or more of the layers, allowing the one or more agents to diffuse through the one or more layers and be delivered to the patient through diffusion. The microneedle array may also include one or more micropores or passageways, whereby the one or more agents pass through the one or more micropores or passageways for delivery to the patient.

In other embodiments, the one or more agents may be located on or about the outer surface of the one or more needles, whereby the one or more agents may be diffuse allowing delivery to the patient. Additionally, the one or more agents may fill partially the microneedle array. In another embodiment, the microneedle array may be made of biodegradable materials that may be broken down releasing the one or more agents for delivery to the patient e.g., the microneedle array may be implanted in a host subcutaneously or the pins of the microneedle array deposited in the skin of the patient.

The present invention may also include an actuator attached operably to the microneedle array, wherein stimulation of the actuator results in the delivery of one or more agents to the patient. The actuator may be operated by a tension force, a manually force, a shear force, a diffusion force, an injection, a pressure, an electrostatic charge, osmosis pressure, a concentration gradient, an electrical field, a magnetic field, a low frequency ultrasound, a high frequency sound or combinations thereof.

The microneedle array may be adapted to penetrate partially a patient subcutaneously. The microneedle array may include one or more needles having one or more tips that may be pointed, rounded, slanted, flared, tapered, blunted or combinations thereof and a portion of the one or more needles may be exposed on the side of the one or more needles. The microneedle array may include one or more layers of a metal, a nonmetal, a polymer, a composite, a resist, a resin, a carbon nano-tube, a nano-sheet, a semiconductor compound, a plastic or combinations thereof.

The present invention provides a method of treating a patient with one or more agents including the step of contacting a microneedle array having one or more agents with a patient, whereby the one or more agents may be delivered to the patient. The microneedle array may further include one or more agents and/or an actuator attached operably to the microneedle array to delivery the one or more agents to the patient. The method of treating a patient with one or more agents, which may be delivered through a pin of the microneedle array to the patient, or through diffusion of the agents deposed on or about the microneedle array. The method of treating a patient may also include the step of stimulating the microneedle array, whereby the stimulation of the microneedle array results in the one or more agents being delivered to the patient. Alternatively, the present invention provides a method of treating a patient including the implanting the microneedle array subcutaneously within the patient.

The present invention also provides a device for administering an agent to a patient including a microneedle array having one or more hollow pins and an actuator attached to the microneedle array. The device may further include one or more agents disposed in or about the microneedle array, whereby the one or more agents may be transported to the patient.

The microneedle array may be used to remove one or more materials from an area including the steps of contacting a microneedle array having one or more needles and one or more compartments with the area and withdrawing the one or more materials from the area into the one or more compartments. The one or more materials may be blood, plasma, urine, semen, saliva, lymph fluid, meningeal fluid, amniotic fluid, glandular fluid, cerebrospinal fluid, cells, tissues, and biopsy samples or combinations thereof.

The present invention may be used to as a delivery system for one or more agents to a patient including a reservoir for containing the one or more agents and a microneedle array in connection with the reservoir. The system may also include an actuator positioned on the reservoir to stimulate the delivery of the one or more agents to a patient. The actuator may be stimulated by surface tension, manually force, shear force, diffusion, injection, pressure, electrostatic force, osmosis, concentration gradient, electrical field, magnetic field, low frequency ultrasound, high frequency sound, or combinations thereof. The stimulation may be controlled by a feedback system, a processor or combinations thereof. Additionally, the microneedle array may provide the area to house the reservoir.

Another example of the present invention includes a microneedle array including an interface region and one or more elongated hollow needles extending from the interface region for permitting movement of a substances therethrough, the one or more elongated hollow needles having a length of between about 200 and 400 µm, the one or more elongated hollow needles having at a diameter of between about 20 and 120 µm and the one or more elongated hollow needles having a wall thickness of between about 10 and 20 µm. However, other embodiments may have diameters (e.g., 1-100, 400-600, 600-800 and 800-1000 µm) and walls of different thickness (e.g., 1-10, 20-40, 40-60, 60-80 and 80-100 µm). Additionally, the microneedle may include one or more agents located on or about the surface of the microarray, within the layers of the microarray, within said one or more elongated hollow needles of the microarray or combinations thereof.

The present invention also includes a method of sampling a patient including the steps of contacting a microneedle array having a reservoir with a patient and sampling the patient. The microneedle array may further include one or more agents. The agents may be deposited on or about the microneedle array, within the microneedle array or combinations thereof. The microneedle array of the present method may also include an actuator attached operably to the microneedle array to delivery the one or more agents to the patient. The method may further include the step of stimulating the microneedle array, whereby the stimulation of the microneedle array results in the one or more agents being delivered to the patient.

Additionally, the present invention contemplates the use of hollow microneedle array devices in the administering of vaccines for use in both active and passive immunization. Immunogenic compositions, proposed to be suitable for use as a vaccine, may be prepared most readily directly from immunogenic proteins and/or peptides.

BRIEF DESCRIPTION OF THE DRAWINGS

For a more complete understanding of the features and advantages of the present invention, reference is now made to the detailed description of the invention along with the accompanying figures and in which:

FIG. 8 is a SEM photomicrograph of a graphite-based X-ray mask;

DETAILED DESCRIPTION OF THE INVENTION

Figure 1:
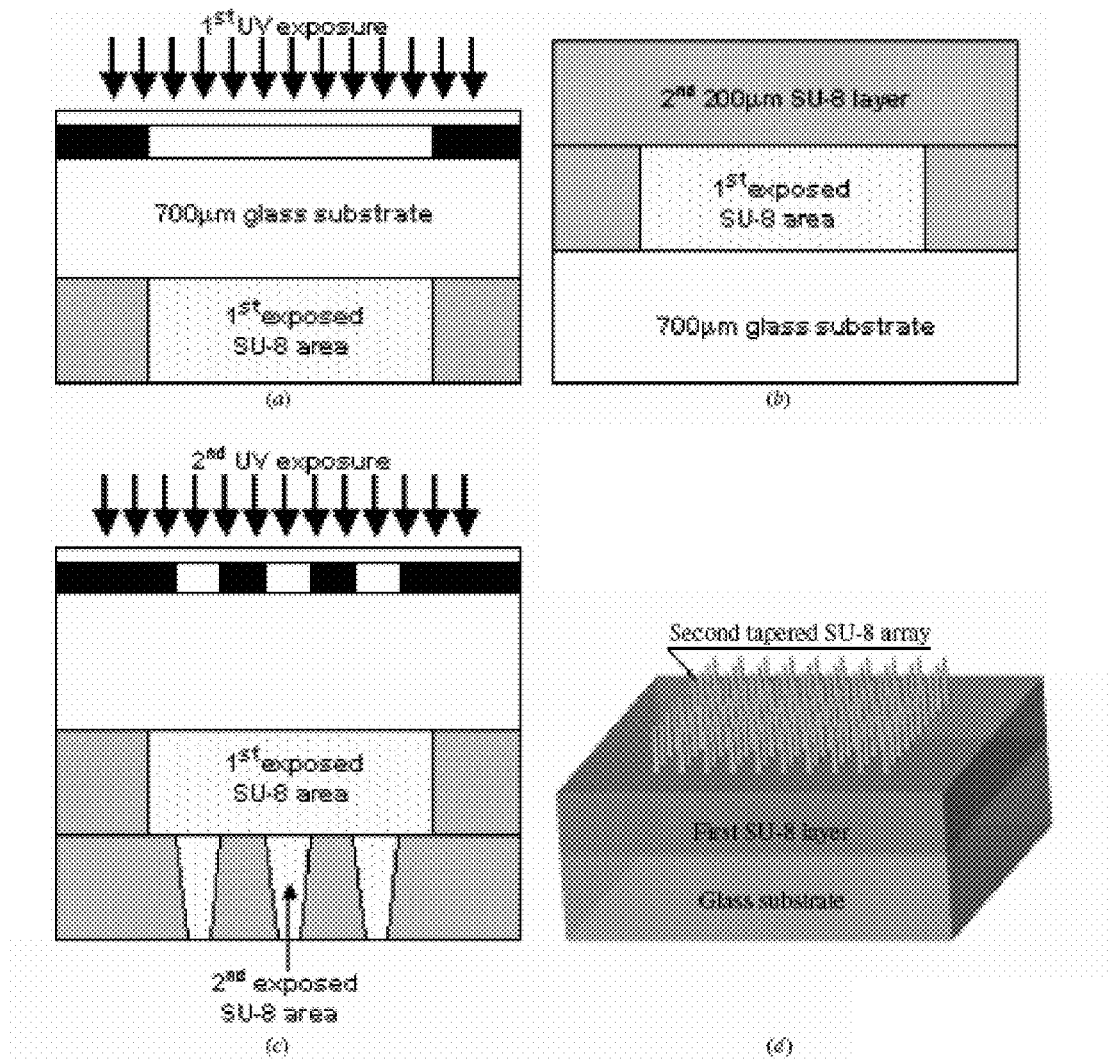
FIG. 1 is a schematic showing the process sequence of the backside exposure of double-layered SU-8.

While the making and using of various embodiments of the present invention may be discussed in detail below, it should be appreciated that the present invention provides many applicable inventive concepts that can be embodied in a wide variety of specific contexts. The specific embodiments discussed herein may be merely illustrative of specific ways to make and use the invention and do not delimit the scope of the invention.

To facilitate the understanding of this invention, a number of terms may be defined below. Terms defined herein have meanings as commonly understood by a person of ordinary skill in the areas relevant to the present invention. Terms such as "a", "an" and "the" may be not intended to refer to only a singular entity, but include the general class of which a specific example may be used for illustration. The terminology herein is used to describe specific embodiments of the invention, but their usage does not delimit the invention, except as outlined in the claims.

As used herein, the term "agent(s)," "active ingredient(s)," "pharmaceutical ingredient(s)," "active agents" and "bioactive agent" are used interchangeably and defined as drugs and/or pharmaceutically active ingredients. The present invention may use or release of, for example, any of the following drugs as the pharmaceutically active agent in a composition: steroids, sympathomimetics, local anesthetics, antimicrobial agents, antihypertensive agents, antihypertensive diuretics, cardiotonics, coronary vasodilators, vasoconstrictors, β-blockers, antiarrhythmic agents, calcium antagonists, anti-convulsants, agents for dizziness, tranquilizers, antipsychotics, muscle relaxants, drugs for Parkinson's disease, respiratory agents, non-steroidal hormones, antihormones, vitamins, antitumor agents, miotics, herb medicines, antimuscarinic, muscarinic cholinergic blocking agents, mydriatics, psychic energizers, humoral agents, antispasmodics, antidepressant drugs, anti-diabetics, anorectic drugs, anti-allergenics, decongestants, antipyretics, antimigrane, anti-malarials, anti-ulcerative, peptides, anti-estrogen, antihormone agents, antiulcer agents, anesthetic agent, drugs having an action on the central nervous system or combinations thereof. Additionally, one or more of the following bioactive agents may be combined with one or more carriers and the present invention (which may itself be the carrier).

Analgesic anti-inflammatory agents such as, acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexamac, piroxicam, phenylbutazone, oxyphenbutazone, clofezone, pentazocine, mepirizole, and the like. Drugs having an action on the central nervous system, for example sedatives, hypnotics, antianxiety agents, analgesics and anesthetics, such as, chloral, buprenorphine, naloxone, haloperidol, fluphenazine, pentobarbital, phenobarbital, secobarbital, amobarbital, cydobarbital, codeine, lidocaine, tetracaine, dyclonine, dibucaine, cocaine, procaine, mepivacaine, bupivacaine, etidocaine, prilocaine, benzocaine, fentanyl, nicotine, and the like. Local anesthetics such as, benzocaine, procaine, dibucaine, lidocaine, and the like.

Antihistaminics or antiallergic agents such as, diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine, chlorpheniramine, and the like. Anti-allergenics such as, antazoline, methapyrilene, chlorpheniramine, pyrilamine, pheniramine, and the like. Decongestants such as, phenylephrine, ephedrine, naphazoline, tetrahydrozoline, and the like.

Antipyretics such as, aspirin, salicylamide, non-steroidal anti-inflammatory agents, and the like. Antimigrane agents such as, dihydroergotamine, pizotyline, and the like. Acetonide anti-inflammatory agents, such as hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin, and the like. Muscle relaxants such as, tolperisone, baclofen, dantrolene sodium, cyclobenzaprine.

Steroids such as, androgenic steroids, such as, testosterone, methyltestosterone, fluoxymesterone, estrogens such as, conjugated estrogens, esterified estrogens, estropipate, 17-β estradiol, 17-β estradiol valerate, equilin, mestranol, estrone, estriol, 17β ethinyl estradiol, diethylstilbestrol, progestational agents, such as, progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-α hydroxyprogesterone, dydrogesterone, dimethisterone, ethinylestrenol, norgestrel, demegestone, promegestone, megestrol acetate, and the like.

Respiratory agents such as, theophilline and $β_2$-adrenergic agonists, such as, albuterol, terbutaline, metaproterenol, ritodrine, carbuterol, fenoterol, quinterenol, rimiterol, solmefamol, soterenol, tetroquinol, and the like. Sympathomimetics such as, dopamine, norepinephrine, phenylpropanolamine, phenylephrine, pseudoephedrine, amphetamine, propylhexedrine, arecoline, and the like.

Antimicrobial agents including antibacterial agents, antifungal agents, antimycotic agents and antiviral agents; tetracyclines such as, oxytetracycline, penicillins, such as, ampicillin, cephalosporins such as, cefalotin, aminoglycosides, such as, kanamycin, macrolides such as, erythromycin, chloramphenicol, iodides, nitrofrantoin, nystatin, amphotericin, fradiomycin, sulfonamides, purrolnitrin, clotrimazole, miconazole chloramphenicol, sulfacetamide, sulfamethazine, sulfadiazine, sulfamerazine, sulfamethizole and sulfisoxazole; antivirals, including idoxuridine; clarithromycin; and other anti-infectives including nitrofurazone, and the like.

Antihypertensive agents such as, clonidine, α-methyldopa, reserpine, syrosingopine, rescinnamine, cinnarizine, hydrazine, prazosin, and the like. Antihypertensive diuretics such as, chlorothiazide, hydrochlorothrazide, bendoflumethazide, trichlormethiazide, furosemide, tripamide, methylclothiazide, penfluzide, hydrothiazide, spironolactone, metolazone, and the like. Cardiotonics such as, digitalis, ubidecarenone, dopamine, and the like. Coronary vasodilators such as, organic nitrates such as, nitroglycerine, isosorbitol dinitrate, erythritol tetranitrate, and pentaerythritol tetranitrate, dipyridamole, dilazep, trapidil, trimetazidine, and the like. Vasoconstrictors such as, dihydroergotamine, dihydroergotoxine, and the like. β-blockers or antiarrhythmic agents such as, timolol pindolol, propranolol, and the like. Humoral agents such as, the prostaglandins, natural and synthetic, for example $PGE_1$, $PGE_2α$, and $PGF_2α$, and the $PGE_1$ analog misoprostol. Antispasmodics such as, atropine, methantheline, papaverine, cinnamedrine, methscopolamine, and the like.

Calcium antagonists and other circulatory organ agents, such as, aptopril, diltiazem, nifedipine, nicardipine, verapamil, bencyclane, ifenprodil tartarate, molsidomine, clonidine, prazosin, and the like. Anti-convulsants such as, nitrazepam, meprobamate, phenytoin, and the like. Agents for dizziness such as, isoprenaline, betahistine, scopolamine, and the like. Tranquilizers such as, reserprine, chlorpromazine, and antianxiety benzodiazepines such as, alprazolam, chlordiazepoxide, clorazeptate, halazepam, oxazepam, prazepam, clonazepam, flurazepam, triazolam, lorazepam, diazepam, and the like. Antipsychotics such as, phenothiazines including thiopropazate, chlorpromazine, triflupromazine, mesoridazine, piperracetazine, thioridazine, acetophenazine, fluphenazine, perphenazine, trifluoperazine, and other major tranqulizers such as, chlorprathixene, thiothixene, haloperidol, bromperidol, loxapine, and molindone, as well as, those agents used at lower doses in the treatment of nausea, vomiting, and the like.

Drugs for Parkinson's disease, spasticity, and acute muscle spasms such as levodopa, carbidopa, amantadine, apomorphine, bromocriptine, selegiline (deprenyl), trihexyphenidyl hydrochloride, benztropine mesylate, procyclidine hydrochloride, baclofen, diazepam, dantrolene, and the like. Respiratory agents such as, codeine, ephedrine, isoproterenol, dextromethorphan, orciprenaline, ipratropium bromide, cromglycic acid, and the like. Non-steroidal hormones or antihormones such as, corticotropin, oxytocin, vasopressin, salivary hormone, thyroid hormone, adrenal hormone, kallikrein, insulin, oxendolone, and the like. Vitamins such as, vitamins A, B, C, D, E and K and derivatives thereof, calciferols, mecobalamin, and the like for dermatologically use. Enzymes such as, lysozyme, urokinaze, and the like. Herb medicines or crude extracts such as, Aloe vera, and the like.

Antitumor agents such as, 5-fluorouracil and derivatives thereof, krestin, picibanil, ancitabine, cytarabine, and the like. Anti-estrogen or anti-hormone agents such as, tamoxifen or human chorionic gonadotropin, and the like. Miotics such as pilocarpine, and the like. Cholinergic agonists such as, choline, acetylcholine, methacholine, carbachol, bethanechol, pilocarpine, muscarine, arecoline, and the like. Antimuscarinic or muscarinic cholinergic blocking agents such as, atropine, scopolamine, homatropine, methscopolamine, homatropine methylbromide, methantheline, cyclopentolate, tropicamide, propantheline, anisotropine, dicyclomine, eucatropine, and the like.

Mydriatics such as, atropine, cyclopentolate, homatropine, scopolamine, tropicamide, eucatropine, hydroxyamphetamine, and the like. Psychic energizers such as 3-(2-aminopropy)indole, 3-(2-aminobutyl)indole, and the like. Antidepressant drugs such as, isocarboxazid, phenelzine, tranylcypromine, imipramine, amitriptyline, trimipramine, doxepin, desipramine, nortriptyline, protriptyline, amoxapine, maprotiline, trazodone, and the like.

Anti-diabetics such as, insulin, and the like and anticancer drugs such as, tamoxifen, methotrexate, and the like. Anorectic drugs such as, dextroamphetamine, methamphetamine, phenylpropanolamine, fenfluramine, diethylpropion, mazindol, phentermine, and the like. Anti-malarials such as, the 4-aminoquinolines, alphaaminoquinolines, chloroquine, pyrimethamine, and the like. Anti-ulcerative agents such as, misoprostol, omeprazole, enprostil, and the like. Antiulcer agents such as, allantoin, aldioxa, alcloxa, N-methylscopolamine methylsuflate, and the like. The drugs mentioned above may be used in combination as required. Moreover, the above drugs may be used either in the free form or, if capable of forming salts, in the form of a salt with a suitable acid or base. If the drugs have a carboxyl group, their esters may be employed.

The acid mentioned above may be an organic acid, for example, methanesulfonic acid, lactic acid, tartaric acid, fumaric acid, maleic acid, acetic acid, or an inorganic acid, for example, hydrochloric acid, hydrobromic acid, phosphoric acid or sulfuric acid. The base may be an organic base, for example, ammonia, triethylamine, or an inorganic base, for example, sodium hydroxide or potassium hydroxide. The esters mentioned above may be alkyl esters, aryl esters, aralkyl esters, and the like.

As used herein, the term "array," is defined being place in an orderly arrangement this may include a rectangular, circular, oval, polygonal or similarly shaped arrangement of quantities in rows and columns, as in a matrix. The totaling members of the array are 2 or more e.g., an array may be 1 by 2, 1 by 3, 2 by 2, 2 by 3, 10 by 10, 50 by 50, 100 by 100, 200 by 200 and so on.

As used herein, the term "depositing" refers to the placing or setting down of a layer or the laying down or leaving behind by a process. A variety of mechanisms may be used to deposit one or more layers including one or more layers comprising electroplating, vapor deposition, spin coating, coating, sputtering, in-situ polymerization or combinations thereof. The layer may be homogeneous or heterogeneous in nature. Additionally, the layer that is deposited may include a metal, a nonmetal, a polymer, a composite, a resist, a resin, a carbon nano-tube, a plastic or combinations thereof. As used herein, the term "metal" or "metal containing" refers to gold, silver, platinum, copper, aluminum, tungsten, titanium, tantalum, molybdenum, chromium, ruthenium, rhodium, palladium, iridium, nickel or the like, alloy thereof or combinations thereof. The metal compound may be titanium nitride, titanium tungsten, tantalium nitride, tungsten nitride, molybdenum nitride or the like. As used herein, the term "etching" refers to the cut into or removing entirely from a surface.

As used herein, the term "exposing" or "expose" is defined as the removal of a portion of one or more areas. The area may be on a side portion of the one or more pins, on the tip of the pin or combination thereof. The removal may occur through chemical mechanical planarization, planarizing, laser ablation or chemical removal.

As used herein, the term "hollow microneedle array," "needle microarray," "microneedle array" and "microneedle microarray" are used interchangeable and are defined as a small, slender, rod like instrument with a sharp point at one end and a internal volume that may be used in piercing tissues. As used herein, the term "mask," is defined as a pattern of opaque material used to shield selected areas of a surface.

As used herein, the term "material(s)" includes biological samples (e.g., blood, plasma, urine, semen, saliva, lymph fluid, meningeal fluid, amniotic fluid, glandular fluid, cerebrospinal fluid, cells, tissues, and biopsy samples or combinations thereof), chemical compounds (e.g., organic, inorganic vitamins, minerals, and the like).

As used herein, the term "photoimagable polymer(s)" is defined as a photosensitive polymeric substance that are cured by a react with light in a chain-step process and may include the following: photoimagable polyimides, photoimagable benzocyclobutenes, photoimagable epoxies, Novolac based positive photoresists, cardo type photopolymers, and the like. Difunctional epoxy compounds which may be used include diglycidyl ethers of Bisphenol A (e.g., those available under the trade designations "Epon 828", "Epon 1004", "Epon 1001F", "Epon SU-8" and "Epon 1010" from Shell Chemical Co., "DER-331", "DER-332", and "DER-334" from Dow Chemical Co.), 3,4-epoxycyclohexylmethyl-3,4-epoxycyclohexene carboxylate (e.g., "ERL-4221" from Union Carbide Corp.), 3,4-epoxy-6-methylcyclohexylmethyl-3,4-epoxy-6-methylcyclohexene carboxylate (e.g., "ERL-4201" from Union Carbide Corp.), bis(3,4-epoxy-6-methylcyclohexylmethyl) adipate (e.g., "ERL-4289" from Union Carbide Corp.), bis(2,3-epoxycyclopentyl) ether (e.g., "ERL-0400" from Union Carbide Corp.

As used herein, the term "pin(s)" or "needle(s)" is defined as generally a narrow straight cylindrical or roughly cylindrical, and relatively stiff object with a sharp pointed tip. The tip may be pointed, rounded, slanted, flared, tapered, blunt or combinations thereof. The pins may include opening located at the tip, side wall or combinations thereof. Additionally the pin may be porous in nature.

As used herein, the term "resist layer" refers to one or more substances that are deposited on a surface to cover and protect the surface. The resist layer includes a wide variety of photoimagable polymers may be used such as photoimagable polyimides, photoimagable benzocyclobutenes, photoimagable epoxies, novolac based positive photoresists, cardo type photopolymers, and the like. Difuctional epoxy compounds may also be used including diglycidyl ethers of bisphenol A (e.g., those available under the trade designations "Epon 828", "Epon 1004", "Epon 1001F", "Epon SU-8" and "Epon 1010" from Shell Chemical Co., "DER-331", "DER-332", and "DER-334" from Dow Chemical Co.), 3,4-epoxycyclohexylmethyl-3,4-epoxycyclohexene carboxylate (e.g., "ERL-4221" from Union Carbide Corp.), 3,4-epoxy-6-methylcyclohexylmethyl-3,4-epoxy-6-methylcyclohexene carboxylate (e.g., "ERL-4201" from Union Carbide Corp.), bis(3,4-epoxy-6-methylcyclohexylmethyl) adipate (e.g., "ERL-4289" from Union Carbide Corp.), bis(2,3-epoxycyclopentyl) ether (e.g., "ERL-0400" from Union Carbide Corp). As used herein, the term "biodegradable polymers" is defined as polymers that are capable of being decomposed by biological agents. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone).

As used herein, the term "substrate," is defined as an underlying layer and the surface on which a material is deposited. The substrate may be partially transparent substance including glass, plastic, polymer, quartz or combinations thereof. The substrate may include one or more bioactive agents, biodegradable, electrically conductive, thermally conductive, porous, stimulatable, or combinations thereof.

The present invention may be used to deliver agents to a patient e.g., parenterally, intraperitoneally, intraspinally, intravenously, intramuscularly, intravaginally, intraorbital, subcutaneously, or intracerebrally. Dispersions may be prepared in liquid, solid, gel, gas and mixtures thereof. Under ordinary conditions of storage and use, these preparations may contain a preservative to prevent the growth of microorganisms.

Pharmaceutical compositions suitable for the present invention use include sterile aqueous solutions (where water soluble) or dispersions and sterile powders for the extemporaneous preparation of sterile solutions or dispersion. The carrier may be a solvent or dispersion medium containing, for example, water, ethanol, poly-ol (for example, glycerol, propylene glycol, and liquid polyethylene glycol, and the like), suitable mixtures thereof, and vegetable oils.

The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the compositions may be brought about by including in the composition an agent that delays absorption, for example, aluminum monostearate or gelatin.

Sterile solutions may be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier that contains a basic dispersion medium and the required other ingredients from those enumerated above. In the case of sterile powders for the preparation of sterile solutions, the methods of preparation may include vacuum drying, spray drying, spray freezing and freeze-drying that yields a powder of the active ingredient (i.e., the therapeutic compound) plus any additional desired ingredient from a previously sterile-filtered solution thereof.

The present invention may use parenteral compositions formulated in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a subject.

The present invention may administer aqueous compositions that may include an effective amount of the nanoparticle, nanofibril or nanoshell or chemical composition dissolved and/or dispersed in a pharmaceutically acceptable carrier and/or aqueous medium. The biological material should be extensively dialyzed to remove undesired small molecular weight molecules and/or lyophilized for more ready formulation into a desired vehicle, where appropriate. The active compounds may generally be formulated for parenteral administration. The preparation of an aqueous compositions that contain an effective amount of the nanoshell composition as an active component and/or ingredient will be known to those of skill in the art in light of the present disclosure. Typically, such compositions may be prepared as either a liquid solution and/or suspensions; solid forms suitable for using to prepare solutions and/or suspensions upon the addition of a liquid prior to use may also be prepared; and/or the preparations may also be emulsified.

The pharmaceutical forms suitable for delivery using the present invention include sterile aqueous solutions and/or dispersions; formulations including sesame oil, peanut oil and/or aqueous propylene glycol; and/or sterile powders for the extemporaneous preparation of sterile solutions and/or dispersions. It must be stable under the conditions of manufacture and/or storage and/or must be preserved against the contaminating action of microorganisms, such as bacteria and/or fungi.

Solutions of the active compounds as free base and/or pharmacologically acceptable salts may be prepared in water suitably mixed with a surfactant, such as hydroxypropylcellulose. Dispersions may also be prepared in glycerol, liquid polyethylene glycols, and/or mixtures thereof and/or in oils. Under ordinary conditions of storage and/or use, these preparations contain a preservative to prevent the growth of microorganisms.

As used herein, the present invention provides an apparatus, system, method of use, and method of making a hollow metallic microneedle array using backside exposure of a resist layer, and analytic solutions of critical buckling of a tapered microneedle array.

Hypodermic syringes with a hollow pointed microneedle have been one of the most commonly used body fluid extraction, vaccination and medication devices since their insertion by Pravaz and Wood back in the 1850s [1]. While there have been many variations in materials and methods of providing safety, hypodermic syringe design itself has changed very little from its first use. Conventional hypodermic needles create fear of injection-related pain among patients and there has been increasing concern about the risks of transmitting blood born pathogens such as HIV (human immunodeficiency virus) or hepatitis to health-c may be workers by accidental needle stick injuries [2]. In the US, approximately one million needle stick injuries may be reported annually.

Recently, there have been many investigations on the development of alternative designs of hypodermic needles with a goal of creating safer and minimally invasive transdermal drug delivery and body fluid sampling devices. Mitragotri, et al., [3] used low-frequency ultrasound to increase the permeability of human skin by several orders of magnitude compared to the case without ultrasound activation and demonstrated transdermal delivery of high molecular weight proteins such as insulin, interferon gamma and erythropoeitin.

The present invention is an apparatus and method that allows fabrication of hollow metallic microneedle arrays. The microneedle array may be used both as a device for minimally invasive transdermal drug delivery or body fluid sampling through a human skin and as a part of a more complex biological detection/delivery system. The invention herein discloses a novel microfabrication process for a tapered hollow metallic microneedle array using backside exposure of photosensitive polymer.

The present invention provides a metallic, high aspect ratio microstructure (HARM) fabrication technology for injection molding and hot embossing of plastic microfluidic components. Another aspect of the present invention includes a novel method for rapid replication of high precision polymeric and metallic high aspect ratio microstructures using polydimethylsiloxane (PDMS). For the microneedle array, a novel fabrication method of creating tapered metallic hollow microneedle array has been developed. There have been many investigations on the development of alternative designs and methods of hypodermic needles with goals of providing safer, less painful, and minimally invasive transdermal drug delivery and body fluid sampling devices. One of such trends was to build microneedles made of silicon, metal, polymer, and ceramic using micromachining technology. Microneedles are short (~200 μm) enough not to disturb nerves but long enough to penetrate stratum corneum and epidermis of human skin. To date, microneedles fabricated using bulk silicon etching, deep reactive ion etching, LIGA techniques have been investigated. Most of previously investigated microneedles have not been used to produce commercial products mainly due to process complexity. The invention herein discloses a novel method which is a low cost mass production compatible process.

In one embodiment, a high-aspect-ratio an array of tapered polymer (such as SU-8) pillars by ultraviolet (UV) exposure from the backside of the UV-transparent substrates (such as glass) is created. Then, electroplating is carried out to conformally deposit a layer of metal on top of the array of the tapered polymer pillars. The tips of the pillars are polished and the polymer pillars are removed leaving a tapered hollow metallic microneedle array. This novel fabrication method is simple and straightforward compared to previous approaches and is a low cost and mass production compatible approach.

The present invention provides a novel fabrication process for a hollow metallic microneedle array using backside exposure of a resist layer, and analytic solutions of critical buckling of a tapered microneedle array. In one example, a resist layer mesa was formed on a glass substrate and another resist layer, which was spun on top of the resist layer mesa, was exposed through the backside of the glass substrate. An array of resist layer tapered pillar structures, with angles in the range of about 3.1° to 5°, was formed on top of the resist layer mesa. Conformal electrodeposition of metal was carried out followed by a mechanical polishing using a planarizing polymeric layer. All organic layers were then removed to create a metallic microneedle array. In another example, the hollow microneedle array included a fluidic reservoir on the backside of the array. Other examples include both 200 μm and 400 μm tall, 10 by 10 microarrays of metallic microneedles with inner diameters of the tip in the range of about 33.6 to 101 μm and wall thickness of 10 to 20 μm. Analytic solutions of the critical buckling of arbitrary-angled truncated cone-shaped columns may be also presented. A single 400 μm tall hollow cylindrical microneedle made of electroplated nickel with a wall thickness of about 20 μm, a tapered angle of about 3.08° and a tip inner diameter of about 33.6 μm has a critical buckling force of about 1.8 N. Analytic solution can be used for oval, polygonal, square or rectangular cross-sectioned column structures with proper modifications.

One aspect of the present invention includes the development of plastic-based components, both continuous hot embossing and injection molding technologies have been chosen to massively replicate high precision plastic microfluidic components. One of the most critical components is metallic micro master mold insert. The present invention provides for a mold insert that is highly precise in dimension and durable to resistant to mechanical wear during the high temperature hot embossing/injection molding processes.

The present invention provides a novel fabrication process for a tapered hollow metallic microneedle array using backside exposure of SU-8, and analytic solutions of critical buckling of a tapered hollow microneedle. In another example, a SU-8 mesa was formed on a Pyrex glass substrate and another SU-8 layer, which was spun on top of the SU-8 mesa, was exposed through the backside of the glass substrate. An array of SU-8 tapered pillar structures, with angles in the range of 3.1° to 5°, was formed on top of the SU-8 mesa. Conformal electrodeposition of metal was carried out followed by a mechanical polishing using a planarizing polymeric layer. All organic layers were then removed to create a metallic hollow microneedle array with a fluidic reservoir on the backside. Both 200 μm and 400 μm tall, 10 by 10 arrays of metallic microneedles with inner diameters of the tip in the range of about 33.6 to 101 μm and wall thickness of about 10 to 20 μm were fabricated. Analytic solutions of the critical buckling of arbitrary-angled truncated cone-shaped columns may be also presented. A single 400 μm tall hollow cylindrical microneedle made of electroplated nickel with a wall thickness of 20 μm, a tapered angle of 3.08° and a tip inner diameter of about 33.6 μm has a critical buckling force of about 1.8 N. Analytic solutions can be used for rectangular cross-sectioned column structures with proper modifications.

Studies have opened the possibility of creating a needleless transdermal drug delivery device. Henry, et al., [4] used silicon micromachining techniques to create an array of sharp solid silicon microstructures with a height of 150 μm and used such microstructures as a microneedle array to demonstrate increased permeability of human skin by up to four orders of magnitude in-vitro. Such structural height ensures that the microneedle array penetrates just beneath the viable epidermis resulting in efficient drug delivery with minimal pain. McAllister, et al., [5] demonstrated both tapered-shaft and straight-shaft hollow metallic microneedle arrays for transdermal drug delivery applications and microcombustion applications. Lin and Pisano [6] demonstrated 1, 3 and 6 mm long single hollow silicon hypodermic microneedles with fully enclosed fluidic channels. Since it is CMOS compatible, it has a great possibility of integration with electronics to realize smart microneedles. Chandrasekaran and Frazier [7] also demonstrated single hollow metallic hypodermic microneedles and their arrays using electroplated palladium, palladium alloys and nickel.

Microneedles and microneedle arrays can be used as stand-alone devices as well as parts of a more complicated biological detection/delivery system. Zimmermann, et al., [8] demonstrated a disposable self-calibrating continuous glucose monitor using hollow microneedles with a porous poly-Si dialysis membrane and enzyme-based flow-through sensor. Ahn, et al., [9] demonstrated a clinical diagnostic system using multiple stacks of disposable functional plastic bio chips with microneedles as body fluid sampling devices.

The present invention provides a new fabrication method of a tapered hollow metallic microneedle array. The present invention includes a method to form a backside exposure of a double layer of SU-8 through a glass substrate. The fabrication process may be low cost, mass production compatible, and is a relatively simple and straightforward process compared to previous approaches. Additionally, the present invention provides an extended analytic solution of the critical buckling of the microneedle structures. The analytic solutions of the critical buckling used in microneedle research were primarily based on a model of fixed-free prismatic columns although the real structures may be typically tapered hollow columns. Such analytic solutions can be used to determine the critical buckling of hollow microneedles.

Backside exposure of the resist layer. SU-8-based UV-LIGA processes may be commonly used to create very thick, high aspect ratio polymeric and/or metallic microstructures. The present invention may also be used with other epoxy resist layers or combinations of different resist layers. The thicker the resist structures, the larger the difference between the UV exposure dose at the top of the resist and the bottom of the resist. Due to such non-uniform UV exposure dose, the top layer may be overexposed and the bottom layer may be relatively underexposed resulting in the variation of the lateral dimensions of the developed resist structures at the top and at the bottom. Since SU-8 is an epoxy-based negative-tone resist, the top structure tends to be wider than the structures at the bottom of SU-8, which is a particularly significant problem when SU-8 is used for creating metallic mold structures. Recently, Peterman, et al., [10] suggested a backside exposure of thick SU-8 through a mask defined on a glass substrate to create a reentrant SU-8 structure for easy metallic mold production.

In accordance with the present invention, a wide variety of photoimagable polymers may be used such as photoimagable polyimides, photoimagable benzocyclobutenes, photoimagable epoxies, Novolac based positive photoresists, cardo type photopolymers, and the like. Difunctional epoxy compounds which may be used include diglycidyl ethers of Bisphenol A (e.g., those available under the trade designations "Epon 828", "Epon 1004", "Epon 1001F", "Epon SU-8" and "Epon 1010" from Shell Chemical Co., "DER-331", "DER-332", and "DER-334" from Dow Chemical Co.), 3,4-epoxycyclohexylmethyl-3,4-epoxycyclohexene carboxylate (e.g., "ERL-422 1" from Union Carbide Corp.), 3,4-epoxy-6-methylcyclohexylmethyl-3,4-epoxy-6-methyl-cyclohexene carboxylate (e.g., "ERL-4201" from Union Carbide Corp.), bis(3,4-epoxy-6-methylcyclohexylmethyl) adipate (e.g., "ERL-4289" from Union Carbide Corp.), bis(2,3-epoxycyclopentyl) ether (e.g., "ERL-0400" from Union Carbide Corp.

One embodiment of the present invention includes the backside exposure of double-layered SU-8 through a Pyrex 7740 glass substrate. Tapered SU-8 pillar array structures were created using a conventional UV mask and contact printing method. A series of masks was designed to have a circular geometry with diameters of 40, 60, 80 and 100 µm. FIGS. 1A to 1D represents a schematic of the process flow of the fabricate of the backside exposure of a tapered double-layered SU-8 microneedle array. FIG. 1A shows a first 200 µm thick SU-8 exposure through a glass substrate. FIG. 1B shows a second 200 µm thick SU-8 layer preparation. FIG. 1C shows the second SU-8 layer exposure through the glass substrate and the exposed first SU-8 layer to create an array of tapered SU-8 structures. FIG. 1D shows a general view of the fabricated double-layered SU-8 on a glass substrate.

The microneedle array was started with a spin-coating of an SU-8 release layer on top of a 3 inch diameter, 700 µm thick Pyrex 7740 glass substrate. A layer of 200 µm thick SU-8 2075 was spin-coated and was left on a flat surface for an hour for stress relaxation. The SU-8 was then baked at 65° C. for 5 min and at 95° C. for 45 min on a hotplate. UV exposure was carried out with a dose of 1000 mJ cm$^{-2}$ and a post-exposure bake was performed at 65° C. for 1 min and 95° C. for 15 min as shown in FIG. 1A. Another 200 µm thick layer of SU-8 was spin-coated on top of the post-exposure-baked first SU-8 layer as shown in FIG. 1B. The double-layered SU-8 was soft-baked and exposed to UV light with two different doses: 1000 mJ cm$^{-2}$ and 1500 mJ cm$^{-2}$ as shown in FIG. 1C. The samples were then developed in a SU-8 developer for approximately 90 min and cleaned in an oxygen plasma (200 W, 100% $O_2$) for about 2 minutes using a reactive ion etcher as shown in FIG. 1D.

Figure 2:
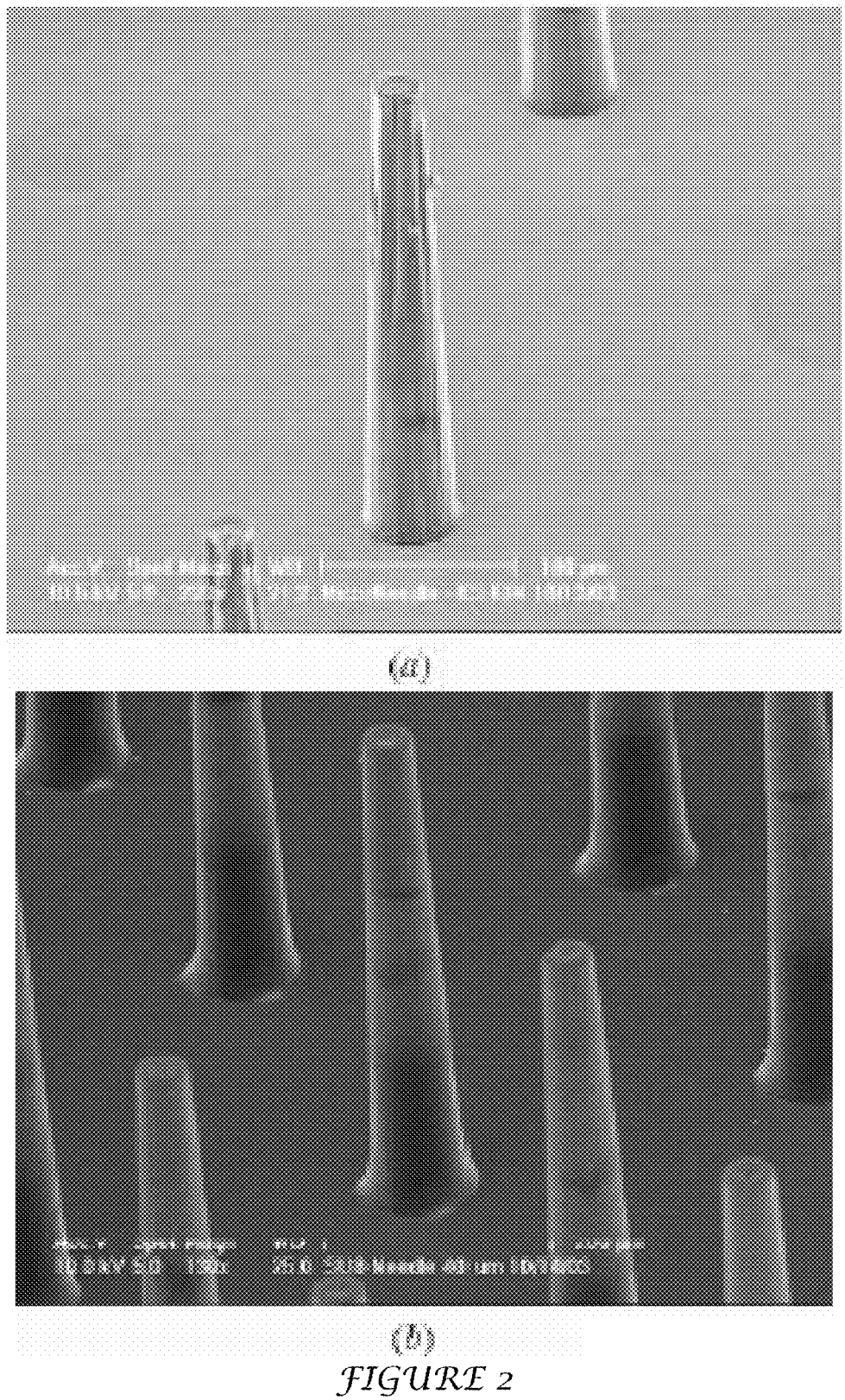
FIG. 2 is a SEM photomicrograph showing the fabrication results of such backside exposed double-layered SU-8 structures.

FIGS. 2A and 2B may be a SEM photomicrograph showing the fabrication results of such backside exposed double-layered SU-8 structures. FIG. 2A shows the result with a dose of 1000 mJ cm$^{-2}$ and FIG. 2B shows the result with a dose of 1500 mJ cm$^{-2}$. With a 1000 mJ cm$^{-2}$ dose, the sidewall of the SU-8 pillar structures was relatively rough due to an insufficient exposure dose. With an increased exposure dose (1500 mJ cm$^{-2}$), the sidewall of the SU-8 pillar structures turned out to be fairly smooth as shown in FIG. 2B and a decent tapered SU-8 pillar structure was formed. An array of SU-8 pillar structures 400 µm in height was also developed with a dose of 2500 mJ cm$^{-2}$.

TABLE 1

Measured dimensions of the 200 µm and 400 µm SU-8 pillar structures.

| Diameters on the mask | Diameters on SU-8 pillars | | | | | |
|---|---|---|---|---|---|---|
| | 200 µm tall SU-8 pillar | | | 400 µm tall SU-8 pillar | | |
| | Bottom | Top | Angle | Bottom | Top | Angle |
| 40 µm | 72.6 µm | 38.0 µm | 4.94° | 76.7 µm | 33.6 µm | 3.08° |
| 60 µm | 95.8 µm | 65.2 µm | 4.37° | 115 µm | 58.2 µm | 4.06° |
| 80 µm | 114 µm | 81.3 µm | 4.67° | 137 µm | 74.3 µm | 4.48° |
| 100 µm | 136 µm | 101 µm | 5.0° | 150 µm | 91.4 µm | 4.19° |

Table 1 shows the measured top and bottom diameters and angles of the 200 µm and 400 µm tall tapered SU-8 pillar structures. For the 200 µm tall SU-8 pillars, angles in the range of about 4.37° to 5° were realized with top diameters in the range of about 38 to 101 µm. For the 400 µm tall SU-8 pillars, angles in the range of about 3.08° to 4.48° were realized with top diameters in the range of about 33.6 to 91.4

µm. The 400 µm tall SU-8 pillars have smaller dimensions at the top and larger dimensions at the bottom compared to those of 200 µm tall SU-8 pillars, due to larger uneven exposure dose distribution through the thicker SU-8.

Figure 3:
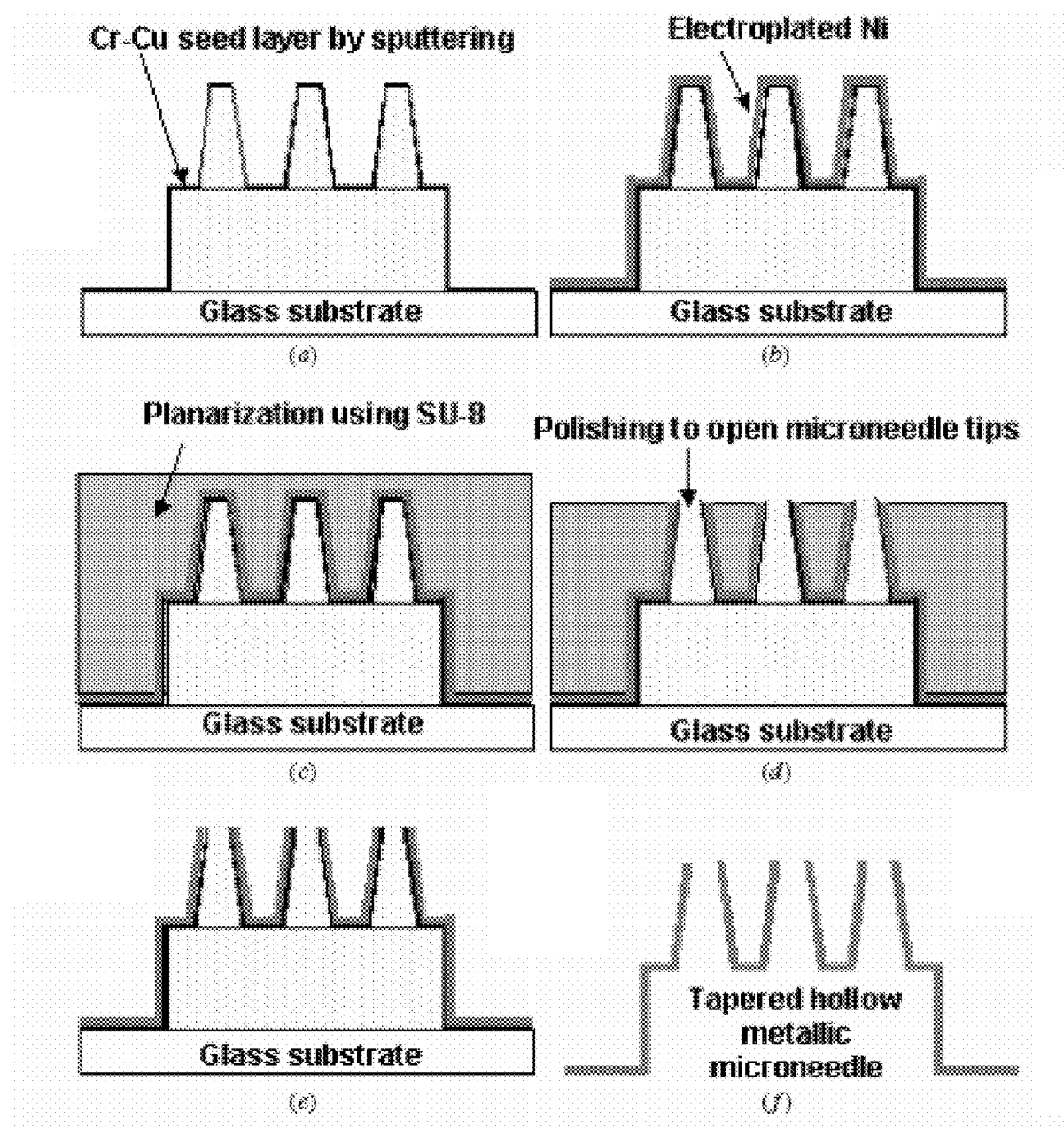
FIG. 3 is a schematic showing the fabrication sequence of the tapered hollow metallic microneedle arrays.
Figure 4:
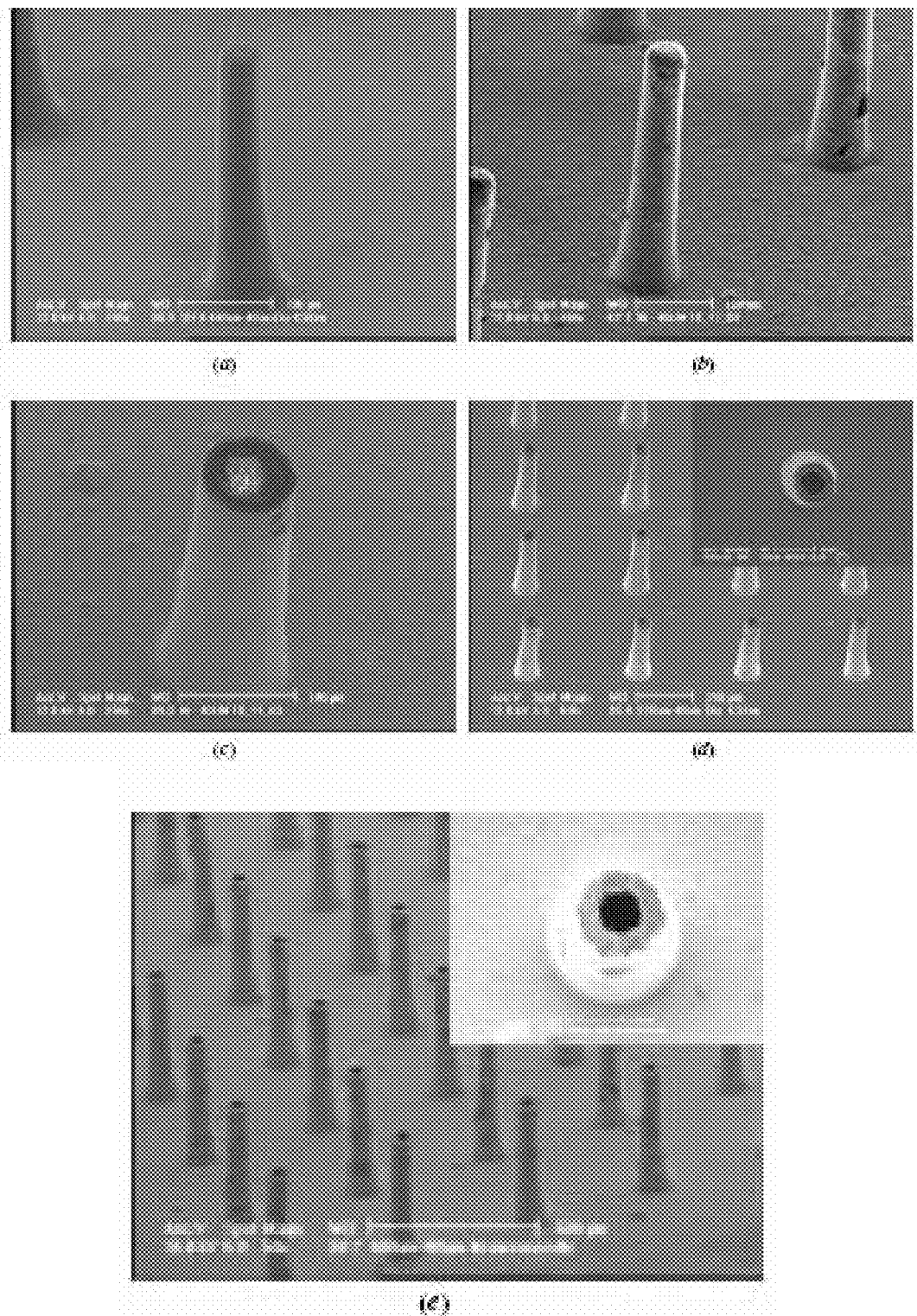
FIG. 4 is a SEM photomicrograph showing a series of SEM photomicrographs of the microneedle array fabrication.

Fabrication of a hollow metallic microneedle array. Based on the double-layered SU-8 backside exposure results, tapered hollow metallic microneedle arrays were fabricated. FIGS. 3A to 3F may be schematics showing the fabrication sequence and FIGS. 4A to 4E may be SEM photomicrographs showing a series of SEM photomicrographs of the microneedle array fabrication. A double-layer (100 Å chromium and 1000 Å copper) electroplating seed was conformally deposited on top of the patterned double-layered SU-8 pillar array structures as shown in FIG. 3A. Nickel electroplating was carried out using a nickel sulfamate bath ($Ni(SO_3NH_2)_2$ 82 g, $H_3BO_3$ 37.5 g and lauryl sulfate 3 g in 1 liter of de-ionized water) at 55° C. with a current density of 5 mA $cm^{-2}$ FIG. 4A shows the SEM photomicrograph of a 400 µm tall tapered SU-8 pillar structure and FIG. 4B shows the same SEM after the nickel electroplating. In order to open the tips of the microneedle array, an additional 450 µm thick SU-8 layer was blanket deposited to provide an organic planarizing layer as shown in FIG. 3C. The SU-8 layer was soft-baked and mechanically polished until the microneedle tips were opened as shown in FIG. 3D and the unexposed planarizing SU-8 layer was removed by dipping in a developer. FIG. 4C shows the SEM photomicrograph of the top view of the opened tip of a microneedle. Next, the SU-8 release layer was stripped off resulting in the separation of electrodeposited nickel coated double-layered SU-8 pillar structures from the glass substrate as shown in FIG. 3E. Finally, the double-layered SU-8 structures were dry etched using $O_2/CF_4$ (80%: 20%) plasma with a power of 500 W using a microwave plasma etch. Followed by a wet etch of the electroplating seed layer resulting in a tapered hollow metallic microneedle array with a fluidic reservoir on the backside as shown in FIG. 3F. FIG. 4D and FIG. 4E show SEM photomicrographs of the 200 µm and 400 µm tall hollow metallic microneedle arrays from the top side. For example, the metallic wall thickness for the 200 µm tall microneedle is about 10 µm and that for the 400 µm tall microneedle is about 20 µm.

Figure 5:
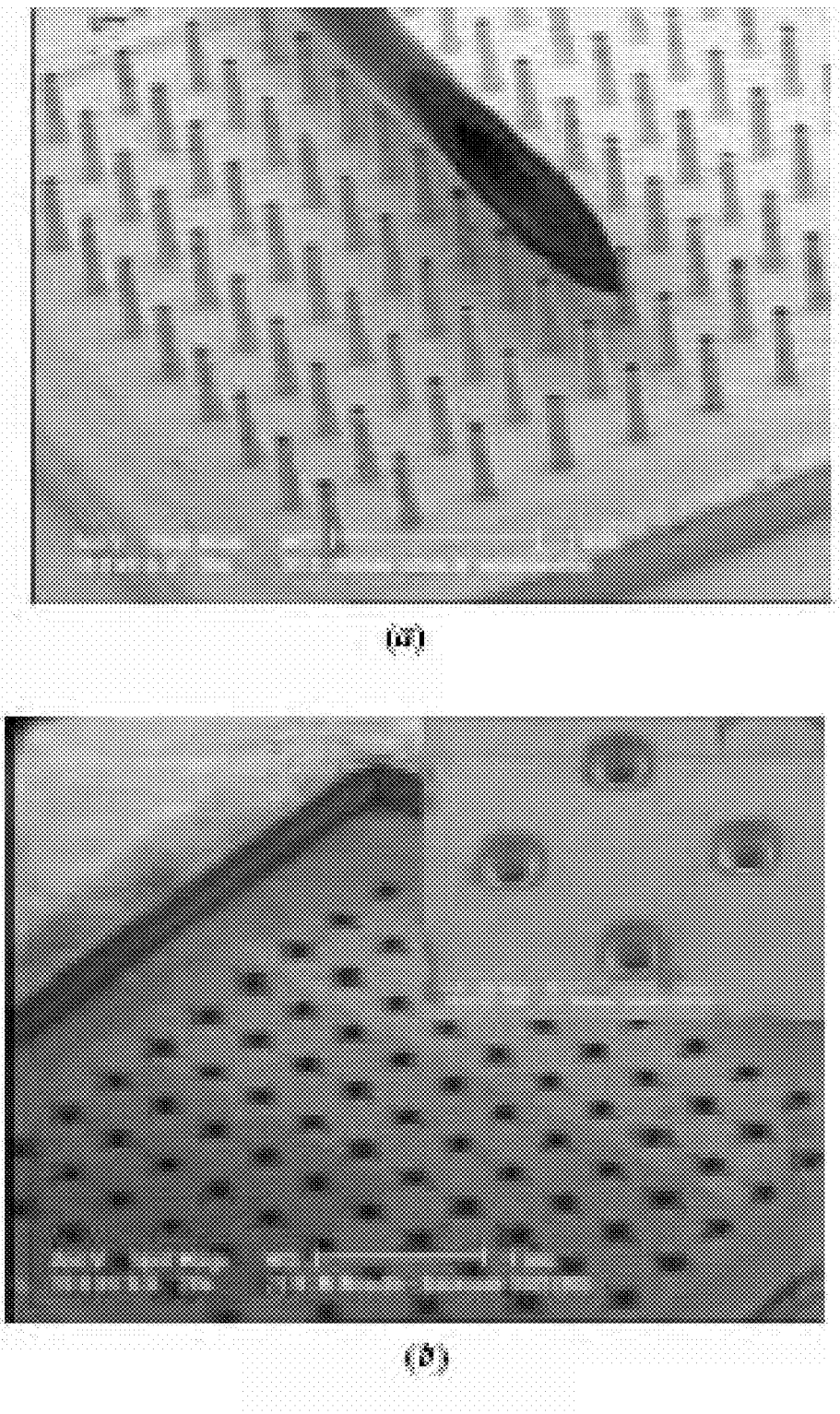
FIG. 5 is a SEM photomicrograph showing a 400 µm tall microneedle array.

FIG. 5A shows a SEM photomicrograph of a 400 µm tall microneedle array with a conventional gauge 28 stainless steel needle and FIG. 5B shows the backside of the hollow microneedle array which shows the fluidic reservoir and holes defined by complete removal of SU-8.

Analytic solution of the critical buckling for a tapered hollow microneedle. A microneedle needs to be mechanically strong enough to penetrate the skin without mechanical failure. Two mechanical failure modes may be of interest in this regard: critical buckling and yield failure. If such failures occur, a small piece of broken needle may be left inside the skin, which may cause biological complications. The yield failure occurs when a load greater than yield strength of the material is applied. The yield strength is an intrinsic material property independent of mechanical geometry. Since microneedles may be typically very high aspect ratio column-like structures, they may be also susceptible to catastrophic buckling failure. Most previous work on microneedles used critical buckling of the fixed-free prismatic column even though they may be fixed-free tapered hollow columns.

Figure 6:
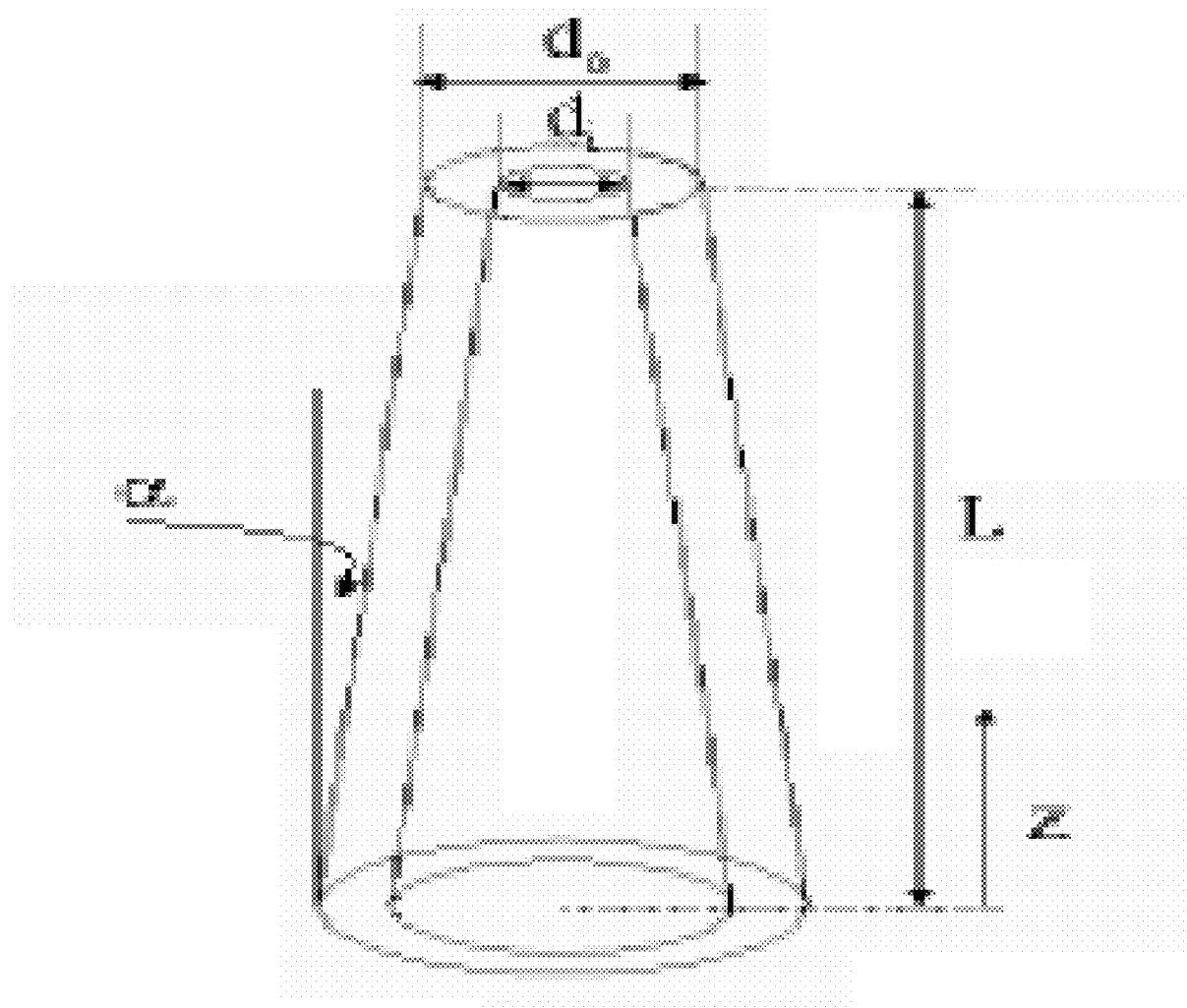
FIG. 6 is a diagram showing a truncated cone column with a structural height.

The present invention includes an analytic solution for critical buckling of the fixed-free tapered hollow truncated cone column. FIG. 6 is a diagram showing a truncated cone column with a structural height L, a tapering angle α, an inner diameter $d_i$ and an outer diameter $d_o$. The column is fixed at the bottom (z=0) and is free at the top (z=L). In order to find the load that causes buckling of the column, one should solve the differential equation:

$$EI(z)\frac{d^2 y(z)}{dz^2} + M(z) = 0,$$

Where E is Young's modulus of the material (assuming that it is homogeneous), I (z) is the moment of inertia about the centroid, y(z) is the assumed deflected shape, M(z) is the bending moment. Smith [11] showed the critical buckling load (Pcr) of the fixed-free tapered column as:

$$P_{cr} = \frac{\pi^2 E}{2L^3} \int_0^L \sum_{i=0}^n k_i z^i \cos^2\left(\frac{\pi z}{2L}\right) dz,$$

Where $k_i z_i = I(z)$ and ki is the constant coefficient which is dependent on the column's cross section. The Equation can be applied to any columnar structure when area moment of inertia of arbitrary cross-sectional shape can be expressed by a polynomial of z. For the case of a hollow truncated cone column with an angle α, inner diameter di and an outer diameter do, the area moment of inertia at any position z is given by:

$$I(z) = \frac{\pi}{64}\begin{bmatrix} (d_o^4 - d_i^4) + 8(L-z)\tan\alpha(d_o^3 - d_i^3) + \\ 24(L-z)^2\tan\alpha^2(d_o^2 - d_i^2) + \\ 32(L-z)^3\tan\alpha^3(d_o - d_i) \end{bmatrix}.$$

Then, the critical buckling load of the truncated hollow cone fixed-free column can be determined as follows:

$$P_{cr} = \frac{E}{80\pi L^2} \times \begin{bmatrix} \frac{5\pi^4}{16}(d_o^4 - d_i^4) + \left(5\pi^2 + \frac{5}{4}\pi^4\right)(d_o^3 - d_i^3)L\tan\alpha + \\ \left(15\pi^2 + \frac{5}{2}\pi^4\right)(d_o^2 - d_i^2)L^2\tan\alpha^2 + \\ \left(-120 + 30\pi^2 + \frac{5}{2}\pi^4\right)(d_o - d_i)L^3\tan\alpha^3 \end{bmatrix}.$$

For a prismatic column with a diameter d, the critical buckling load becomes $$P_{cr} = \frac{E\pi^3 d^4}{256L^2} = \frac{\pi^2 EI}{4L^2}.$$

Figure 7:
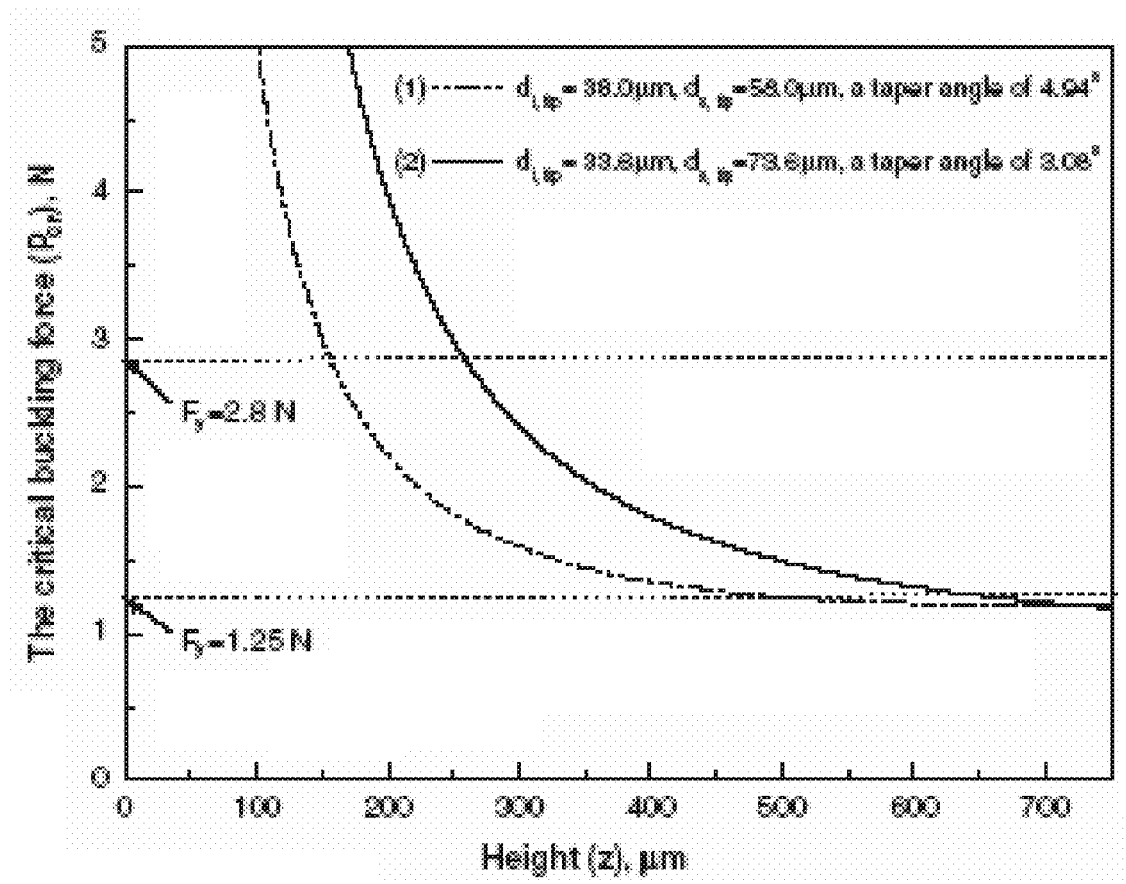
FIG. 7 is a graph showing the critical buckling forces and the yield strength limits as a function of the height of microneedle.

FIG. 7 is a graph of the critical buckling forces and the yield strength limits as a function of the height of microneedle for two different cases: (1) $d_i$=38 µm, $d_o$=58 µm, a taper angle of 4.94° and (2) $d_i$=33.6 µm, $d_o$=73.6 µm, a taper angle of 3.08° at the tip. For a single 400 µm tall electroplated nickel microneedle with a tapered angle of 3.08°, a wall thickness of 20 µm and an inner diameter of the tip of 33.6 µm, the critical buckling force is found to be about 1.8 N based on Young's modulus of the electroplated nickel of 23.1 GPa [12]. Based on the yield strength of 830 MPa [12], the force that reaches the yield strength at the tip of the electroplated nickel hollow microneedle is found to be about 2.8 N.

For example, a single 200 μm tall microneedle with a tapered angle of 4.94°, a wall thickness of 10 μm and an inner diameter of the tip of 38 μm, the critical buckling force is found to be about 2.25 N and the force that reaches the yield strength at the tip is found to be about 1.25 N. FIG. 7 shows the critical buckling forces and the yield strength limits for single electroplated microneedles with dimensions of 200 μm tall (4.94°, 58 μm outer diameter, 38 μm inner diameter at the tip) and 400 μm tall (3.08°, 73.6 μm outer diameter, 33.6 μm inner diameter at the tip). Since our design has 10 by 10 array of microneedles, assuming the uniformly distributed external stress, both buckling force and yield strength limit will be 100 times greater than that of the single microneedle.

Although the critical buckling force is considered a critical parameter of the device design, since the deflection of the microneedle would not be small even with relatively small shear forces and/or eccentric axial loads, more likely causes of mechanical failure of microneedles would be either shear forces or eccentric axial loads. When these forces may be considered, the maximum load should be determined by the maximum amount of the allowable deflection of the microneedle. When an eccentric axial load P (the axial load that is not perfectly along the axis) is applied to the microneedle, the maximum deflection at the tip (δ) is given by $$\delta_{max} = e\left(\sec\sqrt{\frac{P_{max}}{EI}}L - 1\right).$$

Where e is the eccentricity from the center of the axis. When a shear force (V) applies to the tip of the microneedle (assuming that the microneedle is a prismatic column), the maximum deflection at the tip is given by:

$$\delta_{max} = \frac{V_{max}L^3}{3EI}.$$

The analytic solution can be used for other cross-sectional shaped columns (e.g., round, oval, polygonal, and rectangular) with different expressions of the area moment of inertia. The analytic solution can be used for critical buckling analysis of various practical microneedles as well as other common columnar microstructures.

The present invention provides a microneedle array. In one embodiment, the microneedle array is a 10 by 10 tapered hollow electroplated nickel microneedle array with a fluidic reservoir on the backside was realized by backside exposure of double-layered SU-8 through a glass substrate. Other embodiments include both 200 μm tall and 400 μm tall microneedles with tapering angles less than 5 degree. Since the process is rapid, simple and relatively inexpensive in nature, it may be used in the manufacturing of commercial metallic microneedles for painless drug delivery and body fluid sampling. Additionally, metallic microneedles may be used for clinical applications using fabrication methods using biocompatible metals.

Another provision of the present invention includes an extended analytic solution of the critical buckling force of the fixed-free truncated cone column was derived. Such analytic solutions can be used for common microneedle structures and critical buckling analysis of various columnar structures.

The present invention provides for a generic LIGA process and SU-8 based UV-LIGA process. A low cost X-ray mask technology for the LIGA process using two different technologies: a graphite substrate-based X-ray mask technology and a polyimide membrane-based X-ray mask technology. Both X-ray mask technologies may be inexpensive and suitable for general LIGA processes. One example includes the fabrication of a graphite membrane mask which was started with fly cutting and polishing a densified 4-inch diameter graphite disk. Then, Ti/Cu seed layer was sputtered on the graphite. Either SU-8 or thick photoresist (e.g., shipley SJR 5740) was spin cast, patterned, and gold electroplating was carried out through polymer mold to achieve 13 microns or thicker Au absorbers.

FIGS. 8A to 8D may be images of one embodiment of the present invention. FIG. 8A is a SEM photomicrograph of a graphite-based X-ray mask. FIG. 8B is a SEM photomicrograph of 400 μm tall SU-8 structures with aspect ratios of up to 20:1. FIG. 8C is an optical micrograph of the tool used for electroforming of micro mold insert on cylindrical shaft. FIG. 8D is a SEM photomicrograph of electroformed test micro mold insert for continuous hot embossing.

Fabrication of polyimide membrane mask included the mounting of 13 or 25 micron thick Kapton polyimide film on aluminum stretcher. The stretched film was annealed in an oven and followed by a sputtering of Ti/Cu as a seed layer and SU-8 or SJR 5740 patterning. Finally, gold with a thickness of 13 micron or thicker was electroplated.

As an alternative to the LIGA technology, UV-LIGA technology using SU-8 for the fabrication of high precision metallic micro mold insert has also been developed. A variety of test microstructures were fabricated using SU-8 with aspect ratios of up to 20:1 and thickness of 200 μm and 400 μm as shown in FIG. 8B. However, other aspect ratios maybe used 5:1, 10:1 15:1 25:1 and 30:1 in addition to different thickness of about 100, 125, 150, 175, 225, 250, 275, 300, 325, 350, 375, 450, 475 and 500 μm.

Based on the development of base technologies, studies focused on the development of unique micro mold insert that enables continuous hot embossing of micro plastic components. In order to realize such micro mold inserts, a generic technology was developed that can electroform high precision metallic parts on metallic cylindrical shafts. A three-fourths of an inch diameter AISI 316 stainless steel cylinder was used as a substrate. The substrate was cleaned by Wood's strike etching process and thin Ni layer was plated on the sample to get better adhesion and uniform deposits on non-planar substrates. Exposed blank PMMA sheet was developed and rinsed and the PMMA sheet was wrapped around the stainless steel cylinder at 130° C. and clamped using the wrapping tool as shown in FIG. 8C. Electroplating was carried out for the wrapped around PMMA mold and the PMMA mold was removed. FIG. 8D shows an SEM photomicrograph of realized mold insert on stainless steel cylinder.

Figure 9:
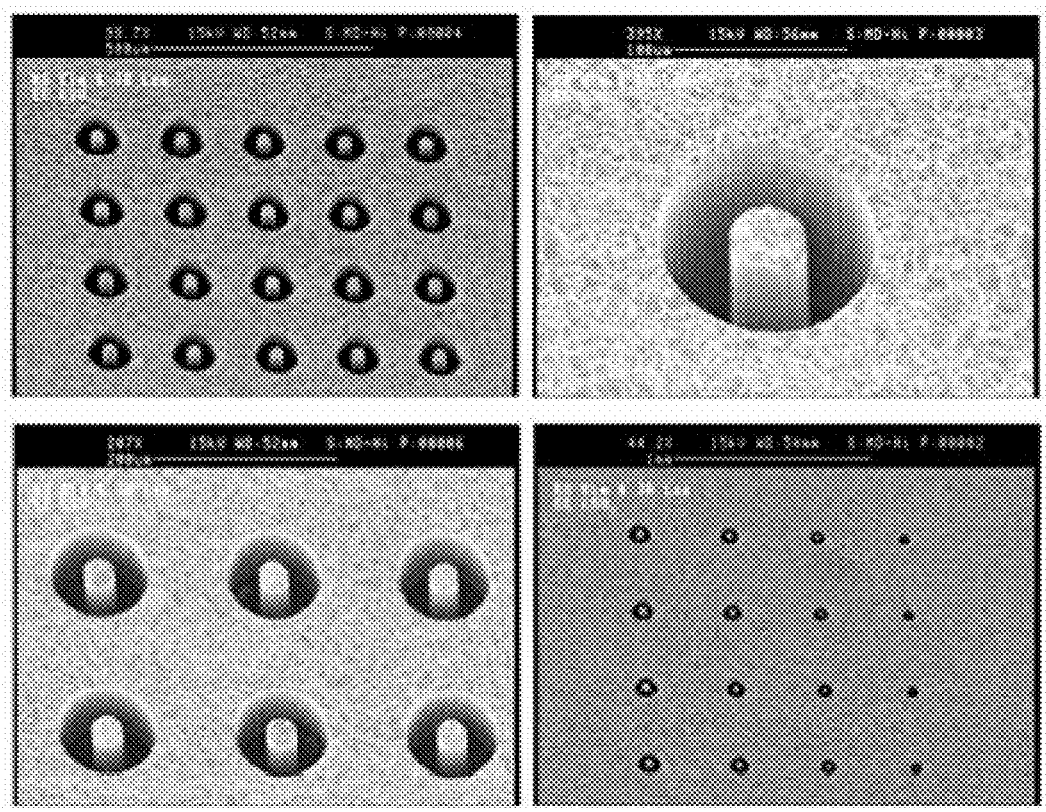
FIG. 9 is a SEM photomicrographs of Ni micro mold insert for plastic microneedle array.

The present invention provides for a LIGA-based metallic micro mold insert for plastic microneedle array replication. In one embodiment, Nickel was used as a substrate material for mold insert for microneedle arrays, however, other metals may be used. The metals used may be metals or metal containing compounds. The metal may be gold, silver, platinum, copper, aluminum, tungsten, titanium, tantalum, molybdenum, chromium, nickel or the like, alloy thereof or combinations thereof. The metal compound may be titanium nitride, tantalum nitride, tungsten nitride, molybdenum nitride or the like. A ground and polished 3-inch diameter Ni plate was activated in C-12 activator for 1 minute at −2 volts to clean the surface and promote the adhesion. Commercially available PMMA sheet (e.g., a thickness of 1 mm or 2 mm) was bonded using MMA bonding solutions and fly cut down to 200 micron. The PMMA sheet was exposed to X-ray and it was developed by four cycles of 20 minute developing and 40 minute rinsing. Ni electroplating was carried out to create Ni metallic micro mold inserts on Ni substrate. Due to the requirement of injection molding, surface of micro mold insert must be smooth. Therefore, the surface of electroplated Ni was polished gently using SiC or alumina powder. FIG. 9 shows SEM photomicrographs of nickel mold insert for microneedle array.

The present invention provides the rigorous cleaning of electroplated high aspect ratio microstructures right before electroplating and over electroplating were found to be useful to strongly bonded to the mold insert substrate. Furthermore, the plastic microneedle array replicated from the LIGA processed metallic microneedle array did not form well. UC developed instantaneous infrared heating on the mold surface during injection molding process to address the formation issue. The tip of the microneedle array was blunt and it was difficult to penetrate skin. A backside exposure based SU-8 process was developed to solve the problem and successfully demonstrated tapered hollow microneedle array.

Figure 10:
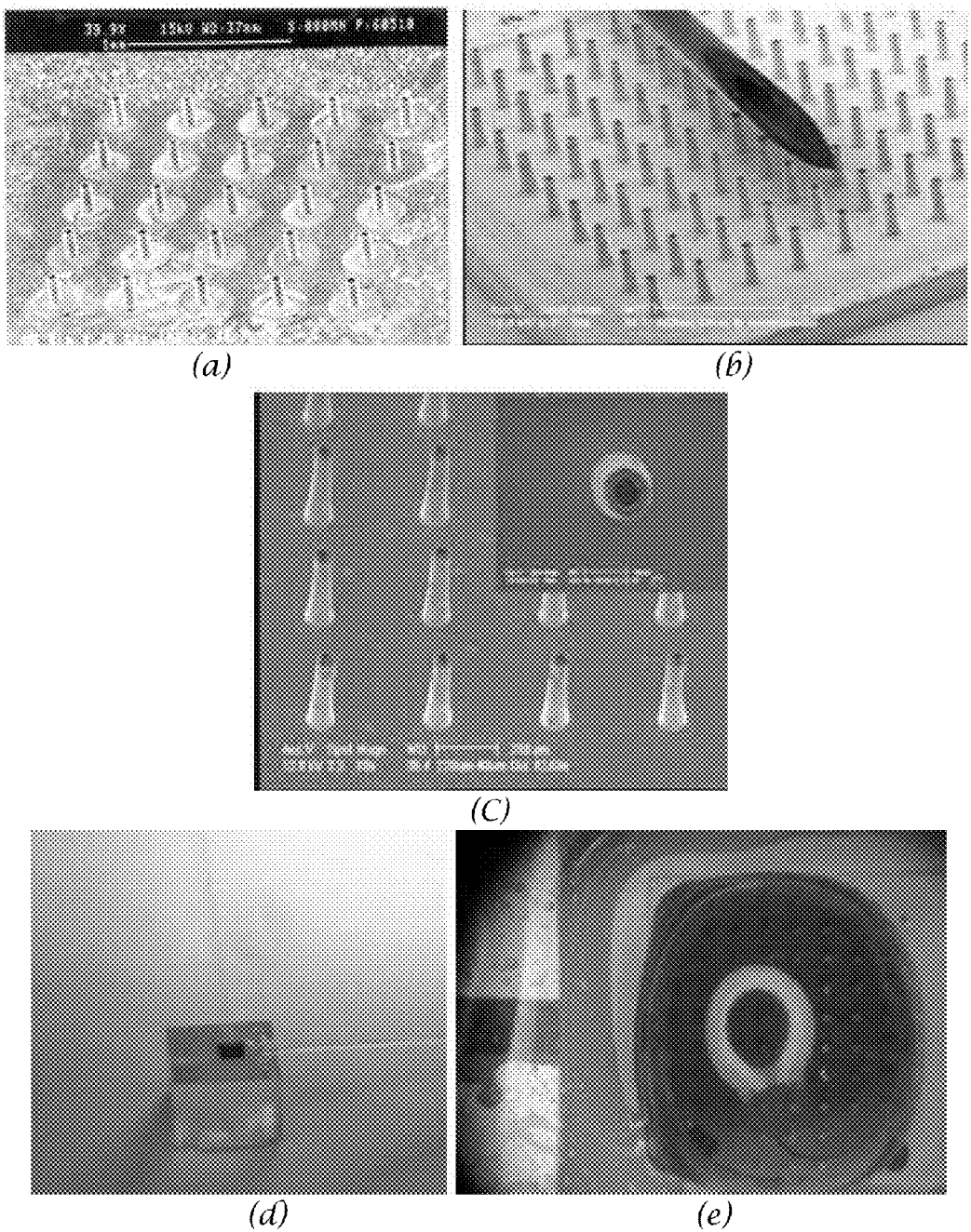
FIG. 10 is a SEM photomicrographs of a microneedle array.

FIG. 10A to 10C may be SEM photomicrographs of a microneedle array. FIG. 10A shows a LIGA processed 300 µm tall microneedle array test structures; FIG. 10B shows a 400 µm tall tapered hollow metallic microneedle array in comparison with a conventional stainless steel needle; FIG. 10C shows a 200 µm tall metallic hollow microneedle array.

Another aspect of the present invention includes the electroplated metallic microneedle arrays investigated by both LIGA and UV-LIGA technologies. A graphite-based X-ray mask based LIGA process was used to demonstrate electroplated metallic microneedle array as shown in FIG. 10a. In order to develop sharper tip needles for easy dermal insertion, SU-8 based UV-LIGA process using the backside exposure were used. An SU-8 mesa was formed on a Pyrex glass substrate and another SU-8 layer, which was spun on top of the SU-8 mesa, was exposed through the backside of the glass substrate. An array of SU-8 tapered pillar structures with angles in the range of about 3.1 and about 5° on top of the SU-8 mesa was formed.

Conformal electrodeposition of metal was carried out followed by a mechanical polishing using a planarizing polymeric layer. All organic layers were then removed to create a metallic hollow microneedle array with a fluidic reservoir on the backside. Both 200 µm and 400 µm tall, 10 by 10 arrays of metallic microneedles with inner diameters of the tip in the range of about 33.6 and about 101 µm and wall thickness of between about 10 and 20 µm were fabricated as shown in FIG. 3b and FIG. 3c. Although other sized arrays may be used such as 5 by 5, 15 by 15, 10 by 20 or nonsymmetric arrangements including 5 by 10, 15 by 10, 15 by 5, 15 by 20 and the like.

One example of an analytic solution of the critical buckling of arbitrary-angled truncated cone shaped columns is presented. It was found that a single 400 µm tall hollow cylindrical microneedle made of electroplated nickel with a wall thickness of 20 µm, a tapered angle of about 3.08°, and a tip inner diameter of 33.6 µm has a critical buckling force of about 1.8 N. SU-8 based microfluidic interconnector was designed specifically for the tapered hollow microneedle array was prepared. A fluidic channel was connected to the backside reservoir. Conventional plastic tubing was used to supply fluids to the microneedle array. Flow rate was measured as a function of applied pressure using red dyed de-ionized water. The flow rate was approximately 90 nL/s-kPa.

The present invention provides for the developed findamental technologies for LIGA and UV-LIGA for the fabrication of plastic and metallic microfluidic components. Such base technologies have been used to provide metallic micro mold inserts for massive replication of polymeric microfluidic structures. In addition, PDMS-based high quality polymeric high aspect ratio microstructure replication technology and tapered hollow microneedle array was developed.

A durable mold insert, rapid heating/cooling of injection molding may be needed to massively produce replicated high aspect ratio polymeric microfluidic components in manufacturing scale. Backside exposure based tapered hollow microneedle is a rather simple and straightforward method to provide high quality transdermal drug delivery device. It has a great potential to be used as a critical component of a fully integrated miniaturized disposable clinical diagnostics system.

Figure 11A:
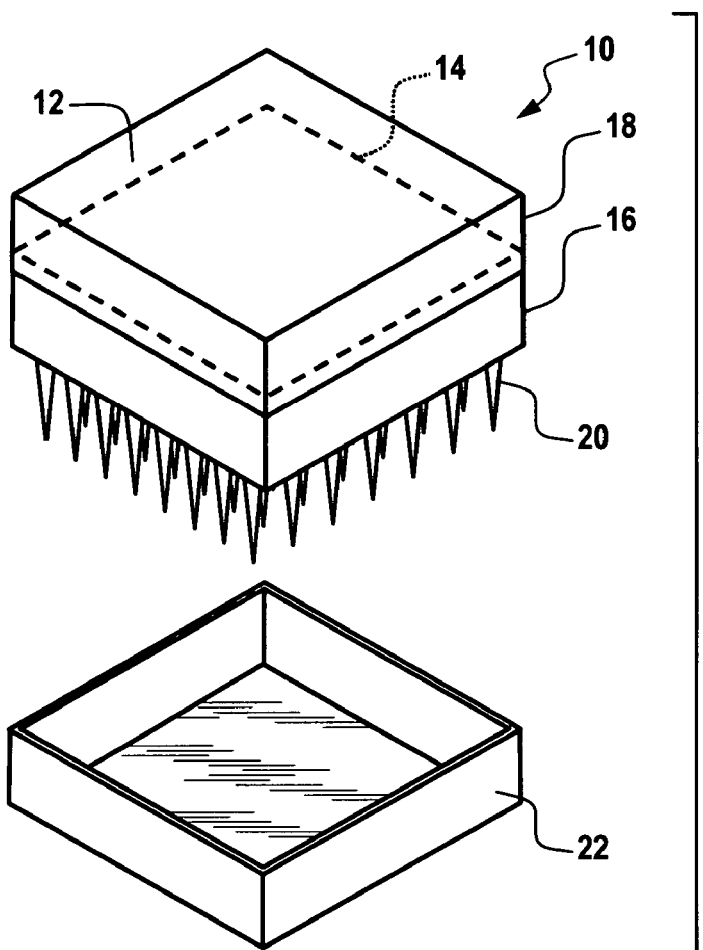
FIG. 11 is a front view of a microneedle array.
Figure 11B:
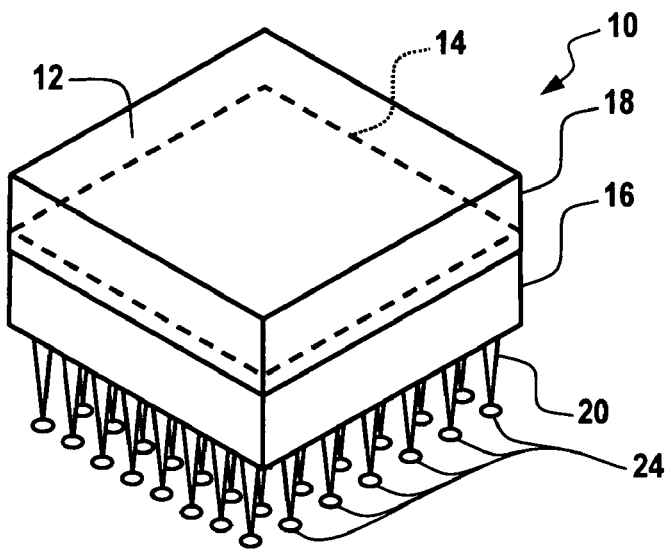

FIG. 11a and FIG. 11b are prospective views of different embodiments of the present invention. The hollow microneedle array device of the present invention includes, in its one embodiment, a reservoir adapted to retain an agent. One example of a hollow microneedle array device 10 shown in FIG. 11a and FIG. 11b include a reservoir 12 defined by an impermeable backing layer 14 and a microneedle array 16. The backing layer and the microneedle array 16 are joined together about the outer periphery of the device, as indicated at 18. The impermeable backing layer 14 may be joined by an adhesive, a heat seal or the like. The hollow microneedle array device 10 also includes a microneedle array pins 20 as one way to deliver an agent to, e.g., the skin of a subject. A release liner 22 is removed prior to use of the device to expose microneedle array pins 20.

The formulation may be retained within the reservoir 12. Alternatively the formulation may be retained within the microneedle array 16, reservoir 12 and/or the microneedle array pins 20 i.e., it deters bulk flow of the formulation out of the reservoir, but allows passage of the formulation from the reservoir through the microneedle array pins 20 into the skin. Materials suitable for use as impermeable backing layer 14 include materials such as polyesters, polyethylene, polypropylene and other synthetic polymers. The material is preferably heat or otherwise sealable to the backing layer to provide a barrier to transverse flow of reservoir contents.

Reservoir 12, defined by the space or gap between the impermeable backing layer 14 and the microneedle array 16, provides a storage structure in which to retain the suspension of agents to be administered. The agent suspension are described in detail herein.

The hollow microneedle array device 10 may also be used to delivery one or more agents transdermally, that is, the pin length is selected to deliver at least a portion of the one or more agents subcutaneously. The microneedle array 16 is made from a pharmaceutically acceptable polymer or metal, such as polydimethylsiloxane, polyisobutylene, polyacrylate, polyurethane and the like or metals, nonmetals, composites, resists, resins, carbon nano-tubes, plastics or combinations thereof. As shown in FIG. 1, hollow microneedle array device 10 is a two dimensional array. It will be appreciated that the hollow microneedle array device 10 can also be a peripheral, or rim array, not shown.

The hollow microneedle array device 10 includes a removable strip or release liner to cover the microneedle array pins 20 and to prevent loss of reservoir contents during storage. Prior to use, the release liner 22 is removed from the device. The release liner 22 is typically a material impermeable to the reservoir contents, for example polyethylene terephthalate, and is releasable usually by treatment with a silicone or fluorocarbon. Another example of a hollow microneedle array device 10 is shown in FIG. 11b. The hollow microneedle array device 10 includes a release cap individually covering each of the microneedle array pins 20.

In the above described embodiments, the devices may be attached to the skin of the user e.g., with adhesive, manually held, although other means for attaching the device to the skin are contemplated and suitable, such as an elastic arm band or an adjustable belt.

The microneedle array 16 may have minimal resistance to diffusion of the reservoir contents. At the same time, the membrane functions to prevent bulk flow the reservoir contents from the device. The reservoir includes agents in suspension, and the agents pass through the microneedle array 16 and through the microneedle array pins 20 that has contacted and penetrated the skin for administration of the entrapped agents. It will be appreciated that the microneedle array 16 can be selected to provide more or less diffusional resistance as desired.

In another embodiment the hollow microneedle array device of the present invention includes a reservoir adapted to retain an agent. One example of a hollow microneedle array device 10 shown in FIG. 11b includes a reservoir 12 defined by an impermeable backing layer 14 and a microneedle array 16. The backing layer and the microneedle array 16 are joined together about the outer periphery of the device, as indicated at 18. The impermeable backing layer 14 may be joined by an adhesive, a heat seal or the like. The hollow microneedle array device 10 also includes a microneedle array pins 20 as one way to deliver an agent to, e.g., the skin of a subject. Individual release caps 24 may be placed over the microneedle array pins 20 for storage and transport and removed prior to use of the device to expose microneedle array pins 20.

The present invention contemplates the use of hollow microneedle array devices in the administering of vaccines for use in both active and passive immunization. Immunogenic compositions, proposed to be suitable for use as a vaccine, may be prepared most readily directly from immunogenic proteins and/or peptides.

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4.578,770, all incorporated herein by reference. The vaccines may be prepared as either a liquid solutions or suspensions: solid forms suitable for solution in, or suspension in, liquid prior to use may also be prepared.

The hollow microneedle array may be used to administer the vaccines parenterally, for example, either subcutaneously or intramuscularly. The active immunogenic ingredient is often mixed with excipients e.g., water, saline, dextrose, glycerol, ethanol, or the like and combinations thereof that are pharmaceutically acceptable and compatible with the active ingredient. In addition, if desired, the vaccine may contain minor amounts of auxiliary substances such as wetting or emulsifying agents, pH buffering agents, or adjuvants which enhance the effectiveness of the vaccines.

The hollow microneedle array of the present invention may be used to administer the vaccines in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. The hollow microneedle array may also be used for initial administration and booster administration.

It will be understood that particular embodiments described herein may be shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents may be considered to be within the scope of this invention and may be covered by the claims.

All publications and patent applications mentioned in the specification may be indicative of the level of skill of those skilled in the art to which this invention pertains. All publications and patent applications may be herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which may be both chemically and physiologically related may be substituted for the agents described herein while the same or similar results would be achieved. All such similar substitutes and modifications apparent to those skilled in the art may be deemed to be within the spirit, scope and concept of the invention as defined by the appended claims.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification, but only by the claims.

REFERENCES

McGrew R. and MeGrew M., Encyclopedia of Medical History (New York: McGraw Hill) (1985).

Jagger J., Hunt E. H., Brand-Elnaggar J. and Person R. D., Rates of needle-stick injury caused by various devices in a university hospital New Engl. J. Med. 319284-8 (1988).

Mitragotri S, Blankschtein D. and Langer R., Ultrasound-mediated transdermal protein delivery Science 269850-31995.

Henry, S., McAllister D. V., Allen, M. G. and Prausnitz, M. R., Micromachined needles for transdermal delivery of drugs Proc. 11th IEEE Int. Conf. MEMS, pp. 494-8 (1998).

McAllister, D. V., Cros, F., Davis, S. P., Matta, L. M., Prausnitz, M. R. and Allen, M. G., Three-dimensional hollow microneedle and microtube arrays $10^{th}$ Int. Conf. Solid-State Sensors and Actuators pp 1098-101 (1999).

Lin L and Pisano A P 1999 Silicon-processed microneedles J. MEMS, pp. 878-84.

Chandrasekaran S and Frazier A B 2003 Characterization of surface micromachined metallic microneedles J. MEMS, pp. 12288-95.

Zimmermann, S., Fienbork, D., Stoeber, B., Flounders, A. W. and Liepmann, D., A microneedle-based glucose monitor:

fabricated on a wafer-level using in-device enzyme immobilization 12th Int. Conf. Solid-State Sensors and Actuators, pp. 99-102 (2003).

Ahn, C., Choi, J., Beaucage, G., Nevin, J., Lee, J. B., Puntambekar, A. and Lee, J.Y. Disposable smart lab-on-a-chip for point-of-c may be clinical diagnostics Proc. IEEE, pp. 92154-73 (2004).

Peterman, M. C., Huie, P., Bloom, D. M. and Fishman, H. A., Building thick photoresist structures from the bottom up. J. Micromech. Micro eng., pp. 13380-2 (2003).

Smith, W. G., Analytic solutions for tapered column buckling. Comput. Struct., pp. 28677-81(1988).

Fritz, T., Leuerer, T., Kruger, C., Mokwa, W. and Schnakenberg, U., Mechanical properties of electroplated nickel Technical Digest of MicroMaterials Micro Mat 3rd Int. Conf. And Exhibition (Berlin, Germany), pp 752-5 (2000).

Kabseog Kim, Daniel S. Park, Hong Lu, W. Che, Kyung Kim, J-B. Lee, and Chong H. Ahn, "A tapered hollow metallic microneedle array using backside exposure of SU-8," Journal of Micromechanics and Microengineering, vol. 14, no. 4, pp. 597-603 (2004).

Kabseog Kim, Sang Won Park, J-B. Lee, Harish Manohara, Yohanes Desta, Michael Murphy, and Chong H. Ahn, "Rapid replication of polymeric and metallic high aspect ratio microstructures using PDMS and LIGA technology," Microsystem Technologies, vol. 9, no. 1-2, pp. 5-10 (2002).

Kab Seog Kim, Sang Won Park, J-B. Lee, Harish Manohara, Yohanes Desta, Michael Murphy, and Chong H. Ahn, "Rapid replication of polymeric and metallic high aspect ratio microstructures using PDMS and LIGA technology," The 4th International Workshop on High Aspect Ratio Microstructure Technology, Baden-Baden, Germany, (2001).

S. W. Park, K. S. Kim, H. Manohara, and J-B. Lee, "Massive replication of polymeric high aspect ratio microstructures using PDMS casting," in *Proceedings of the SPIE* 2001 *Smart Electronics and MEMS*, SPIE vol. 4334, pp. 271-279 Newport Beach, Calif., (March 2001).

J-B. Lee, Sang Won Park, Kabseog Kim, and Harish Manohara, "Methods of rapid reproduction of metallic micromold inserts," U.S. Pat. No. 6,692,680 (February 2004.)

Kabseog Kim, High aspect ratio microstructures and their applications to MEMS, Ph.D., (May 2004).

What is claimed is:

1. A method of making a hollow microneedle array comprising the steps of:
   depositing a first SU-8 layer on a top side of a substrate;
   exposing a bottom side of the substrate to a first UV emission, wherein the UV emission passes through the substrate into the first SU-8 layer to form a first exposed SU-8 area;
   applying a second SU-8 layer of to the first exposed SU-8 area;
   applying one or more masks to the bottom side of the substrate;
   exposing the bottom side of the substrate to a second UV emission, wherein the second UV emission passes through the one or more masks, the substrate and the first exposed SU-8 area to form one or more pins in the second SU-8 layer;
   remove one or more unexposed areas of the second SU-8 layer;
   depositing one or more coating layers on the one or more pins and the first SU-8 layer-to form one or more coated pins;
   removing a portion of the one or more coated pins; and
   separating the one or more coated pins from the one or more pins in the second SU-8 layer to form the hollow microneedle array.

2. The method of claim 1, wherein the substrate is a generally transparent glass substrate.

3. The method of claim 1, wherein the one or more coated pins have a tip that is pointed, rounded, slanted, flared, tapered, blunt or combinations thereof.

4. The method of claim 1, wherein the step of removing a portion of the one or more coated pins occurs on a side portion of the one or more pins.

5. The method of claim 1, wherein the step of removing a portion of the one or more coated pins occurs on a tip of the one or more coated pins.

6. The method of claim 1, wherein the step of removing a portion of the one or more coated pins comprises planarizing, laser ablation or chemical removal.

7. The method of claim 1, wherein the step of depositing one or more coating layers comprises electroplating, vapor deposition, spin coating, coating, sputtering, in-situ polymerization or combinations thereof.

8. The method of claim 1, wherein the one or more coating layers comprise a metal, a nonmetal, a polymer, a composite, a resist, a resin, a carbon nano-tube, a plastic or combinations thereof.

9. The method of claim 1, further comprising the step of applying a release layer between the one or more pins and the substrate.

10. The method of claim 1, further comprising the step of applying a release layer between the one or more pins and the one or more coating layers.

11. The method of claim 1, further comprising the steps of applying a resist layer to the one or more deposited layers, whereby the resist layer covers the one or more deposited layers and the substrate.

12. The method of claim 1, further comprising deposition a resist layer to the one or more coated pins before removing a portion of the one or more coated pins.

13. The method of claim 1, further comprising the steps of etching the hollow microneedle array to remove the second SU-8 layer, wherein a hollow structure remains.

14. The method of claim 1, further comprising the steps of introducing one or more agents into a portion of the hollow microneedle array and the one or more agents are sealed in the hollow microneedle array.

15. The method of claim 14 wherein the one or more agents occupy a volume of between 0.01 µl and 1.0 ml.

16. The method of claim 14 wherein the one or more agents is a solid, liquid or gas.

17. The method of claim 14, wherein the one or more agents may be steroids, sympathomimetics, local anesthetics, antimicrobial agents, antihypertensive agents, antihypertensive diuretics, cardiotonics, coronary vasodilators, vasoconstrictors, β-blockers, antiarrhythmic agents, calcium antagonists, anti-convulsants, agents for dizziness, tranquilizers, antipsychotics, muscle relaxants, drugs for Parkinson's disease, respiratory agents, non-steroidal hormones, antihormones, vitamins, antitumor agents, miotics, herb medicines, antimuscarinic, muscarinic cholinergic blocking agents, mydriatics, psychic energizers, humoral agents, antispasmodics, antidepressant drugs, anti-diabetics, anorectic drugs, anti-allergenics, decongestants, antipyretics, antimigrane, anti-malarials, anti-ulcerative, peptides, anti-estrogen, antihormone agents, antiulcer agents, anesthetic agent, drugs having an action on the central nervous system or combinations thereof.

18. The method of claim 1, further comprising one or more agents disposed in, at, or about the hollow microneedle array.

19. The method of claim 1, wherein the one or more coating layers comprise bioactive agents, biodegradable agents, electrically conductive agents, thermally conductive agents, porous agents, stimulatable agents, or combinations thereof.

20. The method of claim 1, wherein the substrate comprises one or more bioactive agents, biodegradable, electrically conductive, thermally conductive, porous, stimulatable, or combinations thereof.

21. The method of making a hollow microneedle array comprising the steps of:
   forming one or more pins on a substrate, wherein the step of forming one or more pins comprise
   applying a first resist layer to a top side of the substrate,
   masking a portion of the first resist layer,
   irradiating the first resist layer, wherein the unmasked portion of the first resist layer is irradiated to form a first optically cured resist layer,
   applying a second resist layer to the first optically cured resist layer,
   masking a portion of the second resist layer to form one or more masked areas and one or more unmasked areas in the second resist layer, and
   irradiating through the back side of the substrate and the backside of the first cured resist layer and into the one or more unmasked areas of the second resist layer to form one or more optically cured pins in the second resist layer;
   removing one or more uncured areas of the second resist layer;
   depositing one or more coating layers on the one or more optically cured pins and the first optically cured resist layer to form one or more coated pins;
   removing a portion of the one or more coated pins; and
   separating the one or more coated pins from the one or more optically cured pins and the first cured resist layer to form the hollow microneedle array.

22. The method of claim 21, wherein one or more unmasked areas in the second resist layer are generally circular in geometry.

23. The method of claim 21, wherein the one or more unmasked areas in the second resist layer are between about 20 and 120 μm diameter.

24. A method of making a microneedle array comprising the steps of:
   depositing a first layer of SU-8 on a first side of a glass substrate;
   exposing a second side of the glass substrate to a first UV irrediation to form a first cured SU-8 area;
   applying a second layer of SU-8 to the exposed SU-8 area;
   applying one or more masks to the second side of a glass substrate;
   exposing the one or more masks to a second UV irrediation to induce the second layer of SU-8 to form one or more cured pins;
   removing the unexposed second layer of SU-8 to expose the one or more cured pins;
   depositing one or more coating layers on the one or more cured pins to form one or more coated pins, wherein the one or more coating layers comprise a conducting portion;
   a portion of the one or more coated pins; and
   separating the one or more coated pins from the one or more cured pins to form the hollow microneedle array.

25. The method of claim 24, wherein the conducting portion is a wire, molecular wire, polymer, nano-tube, inorganic compound, semiconductor particle, fiber optics or combinations thereof.

26. The method of claim 24, further comprising the steps of disposing one or more agents in or about the hollow microneedle array.

27. The method of claim 24, wherein the one or more agent at least fill partially the one or more coated pins of the microneedle array.

28. The method of claim 24, wherein the one or more coating layers comprise bioactive agents, biodegradable agents, electrically conductive agents, thermally conductive agents, porous agents, stimulatable agents, or combinations thereof.

* * * * *